United States Patent [19]

Furutani et al.

[11] Patent Number: 5,015,574

[45] Date of Patent: May 14, 1991

[54] DNA SEQUENCE INVOLVED IN GENE EXPRESSION AND PROTEIN SECRETION, EXPRESSION-SECRETION VECTOR INCLUDING THE DNA SEQUENCE AND THE METHOD OF PRODUCING PROTEINS BY USING THE EXPRESSION-SECRETION VECTOR

[75] Inventors: Yoshio Furutani, Kanagawa; Akira Nakayama, Mobara; Masaru Honjo, Mobara; Hiroaki Shimada, Mobara; Kouichi Kawamura, Mobara; Izumi Mita, Mobara; Akiko Akaoka, Mobara, all of Japan

[73] Assignees: Agency of Industrial Science and Technology; Extra-Ministerial Bureau of Ministry of International Trade and Industry, both of Tokyo, Japan

[21] Appl. No.: 932,587

[22] Filed: Nov. 20, 1986

[30] Foreign Application Priority Data

Nov. 25, 1985 [JP] Japan .................................. 60-262663

[51] Int. Cl.$^5$ ..................... C12N 15/00; C12N 15/63; C12N 15/75
[52] U.S. Cl. ................................ 435/67.1; 435/320.1; 435/172.3; 435/252.31; 536/27; 935/48; 935/60; 935/74
[58] Field of Search ...................... 435/68, 172.3, 320, 435/319, 221, 222, 839; 536/27

[56] References Cited

U.S. PATENT DOCUMENTS

4,711,844 12/1987 Chang .............................. 435/317.1

FOREIGN PATENT DOCUMENTS

| 0121352 | 12/1984 | European Pat. Off. . |
| 0133756 | 3/1985 | European Pat. Off. . |
| 0149241 | 7/1985 | European Pat. Off. . |
| 0151760 | 8/1985 | European Pat. Off. . |
| 58-162291 | 9/1983 | Japan . |
| 59-59190 | 4/1984 | Japan . |
| WO85/03949 | 9/1985 | PCT Int'l Appl. . |

OTHER PUBLICATIONS

Yang et al., "Identification of the Pleiotropic sacQ Gene of *Bacillus subtilis*. *J. Bacteriol.*, vol. 166, No. 1 (Apr. 1986), 113–119.

Tomioka et al., "Cloning, sequencing, and some properties of a novel *Bacillus amyloliquefaciens* gene involved in the increase of extracellular protease activities," *Journal of Biotechnology*, 3, (1985), 85–96.

Takeichi et al., "Cloning of *Bacillus subtilis* α-Amylase Structural Gene in Plasmid pUB110," Agric. Biol. Chem., vol. 47, No. 1, (1983), 159–161.

Marmur, J., "A Procedure for the Isolation of Deoxyribonucleic Acid from Microorganisms," J. Mol. Biol., 3, (1961), 208–218.

Hagihara et al., "Crystalline Bacterial Proteinase," *The Journal of Biochemistry*, vol. 45, No. 3, (1958), 185–194.

Hidetsngu Fuwa, "A New Method for Microdetermination of Amylase Activity By The Use of Amylose As The Substrate," *The Journal of Biochemistry*, vol. 41, No. 1, (1954), 583–603.

Y. Takagi, "Experimental Methods for Gene Manipulation," p. 139.

(List continued on next page.)

Primary Examiner—Richard A. Schwartz
Assistant Examiner—S. L. Nolan
Attorney, Agent, or Firm—Fisher, Christen & Sabol

[57] ABSTRACT

A expression-secretion vector is constructed by using a DNA sequence comprising a DNA fragment obtained by subjecting a DNA sequence consisting of a region involved in the expression of a gene coding for an extracellular enzyme of a bacterium of the genus Bacillus and a region involved in the secretion of the enzyme thus expressed to a deletion in the region involved in the secretion which can enhance the extracellular production of a protein dependent on the DNA fragment. By transforming a host bacterium with a recombinant DNA molecule formed by inserting a DNA fragment comprising a gene coding for a desired protein into the expression-secretion vector and then culturing the transformed host, the extracellular production of the desired protein in a large amount can be accomplished.

33 Claims, 12 Drawing Sheets

OTHER PUBLICATIONS

Takegi et al., "Nucleotide Sequence and Promoter Region for the Neutral Protease Gene from Bacillus stearothermophilus, vol. 163, No. 3, (Sep. 1985), 824–831.
Anagnostopoulos et al., "Requirements for Transformation of Bacillus subtilis," J. Bacteriol., 81, (1961), 741–746.
Fuji et al., "Molecular Cloning of a Thermostable Neutral Protease Gene . . . ", J. Bacteriol., vol. 154, No. 2, (May 1983), 831–837.
Chang et al., "Cloning and expression of heterologous genes in Bacillus subtilis, (NSC Symp. Ser, 4, (1982), 254–62) Chemical Abstracts 100:46295m.
Blobel et al., "Transfer of Proteins Across Membranes," The Journal of Cell Biology, 67, (1975), 835–851.
Williams et al., "Expressions of Escherichia coli trp . . . " Gene, 16, (1981).
Saito et al., "Preparation of Transforming Deoxyribonucleic Acid by Phenol Treatment," Biochem. Biophys. Acta., 72, (1963), 619–629.
Mandel et al., "Calcium–dependent Bacteriophage DNA Infection," J. Mol. Biol., 53, (1970), 159–162.
Horinouchi, "Expression of Information in Gram-positive Bacteria," Tanpakushitu-Kakusan-Koso 28, (1983), 1468–1478.
Moran, Jr. et al., "Nucleotide Sequences that Signal the Initiation of Transcription and Translation in Bacillus subtilis," Mol. Gen. Genet., 186, (1982), 339–346.
David A. Dubnau, et., The Molecular Biology of the Bacilli (New York: Academic Press, 1982), I, pp. 331 and 332.
Goldfarb et al., "Expression of Tn9–derived Chloramphenicol . . . ", Nature, vol. 293, No. 5830, (Sep. 1981), pp. 309–311.
Chang et al., "Expression of Eukaryotic Genes in B. subtilis Using Signals of penP," Molecular Cloning and Gene Regulation in Bacilli, Ganesan et al., eds., (New York: Academic Press, 1982), pp. 159–169.
T. Maniatis, E. Fritsch, J. Sambrook, Molecular Cloning, A Laboratory Manual, (Cold Spring Harbor, NY: Cold Spring Harbor Lab., 1982), pp. 3–5, 51, 52, 270–2.
Honjo et al., "Cloning and expression of the gene for neutral protease of bacillus amyloliquefaciens . . . ", J. Biotechnol., vol. 1, (1984), 265–277.
Vasantha et al., "Genes for Alkaline Protease and Neutral Protease from Bacillus amyloliquefaciens . . . " J. Bacteriol., vol. 159, No. 3, (Sep. 1984), 811–819.
Yang et al., "Cloning of the Neutral Protease Gene of Bacillus subtilis . . . " J. Bacteriol., vol. 160, No. 1, (Oct. 1984), 15–21.
Uehara et al., "Regulation of Neutral Protease Productivity in Bacillus subtilis, Transformation of High Protease Productivity," J. Bacteriol., 119, (1974), 82–81.
Palva et al., "Nucleotide sequence of the promoter and $NH_2$-terminal signal peptide region of the α-amylase gene from Bacillus amyloliquefaciens," Gene, 15, (1981), 43–51.
"Experimental Agricultural Chemistry", pp. 284–285, Asakura Shuppan (1978) with translation.
McLaughlin et al., "Unique Features in the Ribosome Binding Site Sequence of the Gram-positive Staphylococcus aureus β-Lactamase Gene", The Journal of Biological Chemistry, vol. 256, (Nov. 10, 1981), pp. 11283–11291.
Gryczan, T. J. et al., J. Bacteriol., 132, (1978), pp. 317 to 329.
Chang, S. et al., Mol. Gen. Genet., 168, (1978), pp. 111 to 115.
Yamaguchi, K. et al., J. Bacteriol., 119, (1974), pp. 416 to 424.
Birnboim, H. C. et al., Nucleic Acids Res., 7, (1979), pp. 1513 to 1523.
Maxam, H. C. et al., Proc. Natl. Acad. Sci. USA, 7, (1977), pp. 560 to 564.
Ishikawa, E., (ed.), Enzyme Immunoassay, (1981), pp. 67 to 81.
I. R. Lehman, "T4 DNA Polymerase", Method in Enzymology, vol. 29, (1978).
Biochemical Information II, Boehringer Mannheim, pp. 28–30.
Hayashi et al., J. Bio. Chem., vol. 259, No. 16 (1984), pp. 10448 to 10454.
Mezes et al., J. Bio. Chem., vol. 258, No. 18 (1983), pp. 11211 to 12218.
Schaeffer et al., "Contribution a l'etude gnétique de la sporogenése bactérienne," Comptes Rendus, vol. 251, No. 25 (Dec. 19, 1960), pp. 3125–3127.
Saito et al., "DNA–Mediated Transformation in Bacillus subtilis With Special Reference to the Method for Preparing Competent Cells", Journal of General Applied Microbiology, vol. 1, No. 4 (1961), pp. 243–252.

(List continued on next page.)

OTHER PUBLICATIONS

Millet, J., "Characterization of Proteinases Excreted by *Bacillus subtilis* Marburg Strain during Sporulation", *Journal of Applied Bacteriology*, vol. 33, (1970), pp. 207–219.

Laemmli, U. K., "Cleavage of Structural Proteins during the Assembly of the Head of Bacteriophage T4", *Nature*, vol. 227 (Aug. 15, 1970), pp. 680–685.

Higerd et al., "Hyperprotease-Producing Mutants of *Bacillus subtilis*", Journal of Bacteriology, vol. 112, No. 2 (Nov. 1972), pp. 1026–1028.

Hageman et al., "Effects of Mutational Loss of Specific Intracellular Proteases on the Sporulation of Bacillus subtilis," *Journal of Bacteriology*, vol. 114, No. 2 (May 1973), pp. 612–617.

Kunst et al., "Pleiotropic mutations affecting sporulation conditions and the syntheses of extracellular enzymes in Bacillus subtilis 168", *Biochime*, vol. 56 (1974), pp. 1481–1489.

Chemical Abstract 84:27437u of Levy et al., "Evidence of homologous relation between thermolysin and neutral protease A of *Bacillus subtilis*", *Proceedings of the National Academy of Sciences*, vol. 72, No. 11 (1975), pp. 4341–4345.

Yoneda et al., "Mutation of *Bacillus subtilis* Causing Hyperproduction of α-amylase and Protease, and Its Synergistic Effect," *Journal of Bacteriology*, vol. 124, No. 1 (Oct. 1975), pp. 48–54.

Steinmetz et al., "Mapping of Mutations Affecting Synthesis of Exocellular Enzymes in Bacillus subtilis," *Molecular & General Genetics*, vol. 148 (1976), pp. 281–285.

Bolivar et al., "Plasmids of *Escherichia coli* as Cloning Vectors," in: Methods in Enzymology (1979 ed.), vol. 68, pp. 245–267.

Contente et al., "Characterization of Plasmid Transformation in Bacillus subtilis: Kinetic Properties and the Effect of DNA Conformation", *Molecular & General Genetics*, vol. 167 (1979), pp. 251–258.

Uehara et al., "Thermosensitive, Extracellular Neutral Proteases in Bacillus subtilis: Isolation, Characterization, and Genetics", *Journal of Bacteriology*, vol. 139, No. 2 (Aug. 1979), pp. 583–590.

Goeddel et al., "Direct Expression in *Escherichia coli* of a DNA sequence coding for human growth hormone, *Nature*, vol. 281 (Oct. 11, 1979), pp. 544–548.

Gryczan et al., "Molecular Cloning of Heterologous Chromosomal DNA by Recombination between a Plasmid Vector and a Homologous Resident Plasmid in *Bacillus subtilis*", *Molecular & General Genetics*, vol. 177, No. 3 (1980), pp. 459–467.

Mantsala et al., "Extracellular and Membrane-Bound Proteases from Bacillus subtilis," *Journal of Bacteriology*, vol. 141, No. 2, pp. 493–501.

Tanpakushitsu-Kakusan-Koso, vol. 26, No. 13 (1981), pp. 2043–2046.

Tomioka et al., "Abstracts of Papers", *Annual Meeting of the Agricultural Society of Japan*, 1983, p. 33.

Takeichi et al., "Cloning of Bacillus subtilis α-Amylase Structural Gene in Plasmid pUB110", Agricultural and Biological Chemistry, vol. 47, No. 1 (Jan. 1983).

Palva et al., "Secretion of interferon by *Bacillus subtilis*", *Gene*, vol. 22 (1983), pp. 229–235.

Stahl et al., "Replacement of the *Bacillus subtilis* Subtilisin Structural Gene with an In Vitro–Derived Deletion Mutation", *Journal of Bacteriology*, vol. 158, No. 2 (May 1984), pp. 411–418.

Kawamura et al., "Construction of a *Bacillus subtilis* Double Mutant Deficient in Extracellular Alkaline and Neutral Proteases", *Journal of Bacteriology*, vol. 160, No. 1 (Oct. 1984), pp. 442–444.

Manabe et al., "N-Terminal Amino Acid Sequences of Neutral Proteases from *Bacillus amyloliquefaciens* and *Bacillus subtilis:* Identification of a Neutral Protease Gene Cloned in *Bacillus subtilis*", *Agricultural Biological Chemistry*, vol. 49, No. 8 (1985), pp. 2261–2267.

Shimada et al., "The Nucleotide Sequence and Some Properties of the Neutral Protease Gene of *Bacillus amyloliquefaciens*," *Journal of Biotechnology*, vol. 2 (1985), pp. 57–85.

Honjo et al., "Construction of the secretion vector containing the prepro-structure coding region of Bacillus amyloliquefaciens neutral protease gene and secretion of *Bacillus subtilis* α-amylase and human interferon-beta in Bacillus subtilis", *Journal of Biotechnology*, vol. 3, (1985), pp. 73–84.

Ulmanen et al., "Transcription and Translation of Foreign Genes in *Bacillus subtilis* by the Aid of a Secretion Vector", *Journal of Bacteriology*, vol. 162, No. 1 (Apr. 1985), pp. 176–182.

Yamane et al., "*Bacillus subtilis* Secretion Vectors for Proteins and Oligopeptides Constructed from *B. subtilis* α-Amylase Genes" in: Molecular Biology of Microbial Differentiation, American Society for *Microbiology* (1985), pp. 117–123.

Schein et al., "Secretion of Mature IFN—α2 and Accumulation of Uncleaved Precursor by *Bacillus subtilis* Transformed with a Hybrid α-Amylase Signal Sequence-IFN-α2 Gene", *BIO/TECHNOLOGY*, vol. 4 (Aug. 1986), pp. 719–725.

FIG. 1

```
GATCTTAACA TTTTTCCCCT ATCATTTTTC CCGTCTTCAT TTGTCATTTT TTCCAGAAAA
CTAGAATTGT AAAAAGGGGA TAGTAAAAAG GGCAGAAGTA AACAGTAAAA AAGGTCTTTT

AATCGTCATT CGACTCATGT CTAATCCAAC ACGTCTCTCT CGGCTTATCC CCTGACACCG
TTAGCAGTAA GCTGAGTACA GATTAGGTTG TGCAGAGAGA GCCGAATAGG GGACTGTGGC

CCCGCCGACA GCCCGCATGG ACGAATCTAT CAATTCAGCC GCGGAGTCTA GTTTTATATT
GGGCGGCTGT CGGGCGTACC TGCTTAGATA GTTAAGTCGG CGCCTCAGAT CAAAATATAA

GCAGAATGCG AGATTGCTGG TTTATTATAA CAATATAAGT TTTCATTATT TTCAAAAAGG
CGTCTTACGC TCTAACGACC AAATAATATT GTTATATTCA AAAGTAATAA AAGTTTTTCC

GGGATTTATT GTGGGTTTAG GTAAGAAATT GTCTAGTGCT GTAGCCGCTT CCTTTATGAG
CCCTAAATAA CACCCAAATC CATTCTTTAA CAGATCACGA CATCGGCGAA GGAAATACTC

TTTAACCATC AGTCTGCCGG GTGTTCAGGC CGCTGAGAAT CCTCAGCTTA AAGAAAACCT
AAATTGGTAG TCAGACGGCC CACAAGTCCG GCGACTCTTA GGAGTCGAAT TTCTTTTGGA

GACGAATTTT GTACCGAAGC ATTCTTTGGT GCAA
CTGCTTAAAA CATGGCTTCG TAAGAAACCA CGTT
```

FIG. 2

```
GATCCTCTAGAGTCGACCTGCAGCCCA
    GAGATCTCAGCTGGACGTCGGGTTCGA
```

FIG. 3

BamHI cleavage site  HindIII cleavage site

```
GATCTTAACA TTTTCCCCT ATCATTTTTC CCGTCTTCAT TTGTCATTTT TTCCAGAAAA
CTAGAATTGT AAAAAGGGGA TAGTAAAAAG GGCAGAAGTA AACAGTAAAA AAGGTCTTTT

AATCGTCATT CGACTCATGT CTAATCCAAC ACGTCTCTCT CGGCTTATCC CCTGACACCG
TTAGCAGTAA GCTGAGTACA GATTAGGTTG TGCAGAGAGA GCCGAATAGG GGACTGTGGC

CCCGCCGACA GCCCGCATGG ACGAATCTAT CAATTCAGCC GCGGAGTCTA GTTTATATT
GGGCGGCTGT CGGGCGTACC TGCTTAGATA GTTAAGTCGG CGCCTCAGAT CAAAATATAA

GCAGAATGCG AGATTGCTGG TTTATTATAA CAATATAAGT TTTCATTATT TTCAAAAAGG
CGTCTTACGC TCTAACGACC AAATAATATT GTTATATTCA AAAGTAATAA AAGTTTTTCC

GGGATTTATT GTGGGTTTAG GTAAGAAATT GTCTAGTGCT GTAGCCGCTT CCTTTATGAG
CCCTAAATAA CACCCAAATC CATTCTTTAA CAGATCACGA CATCGGCGAA GGAAATACTC

TTTAACCATC AGTCTGCCGG GTGTTCAGGC CGCTGAGAAT CCTCAGCTTA AAGAAAACCT
AAATTGGTAG TCAGACGGCC CACAAGTCCG GCGACTCTTA GGAGTCGAAT TTCTTTTGGA

GACGAATTTT GTACCGAAGC ATTCTTTGGT GCAAGGGATC C
CTGCTTAAAA CATGGCTTCG TAAGAAACCA CGTTCCCTAG G
```

FIG. 7A

```
GATCTTAACA TTTTCCCCT  ATCATTTTTC CCGTCTTCAT TTGTCATTTT TTCCAGAAAA
CTAGAATTGT AAAAGGGGA  TAGTAAAAAG GGCAGAAGTA AACAGTAAAA AAGTCTTTT

AATCGTCATT CGACTCATGT CTAATCCAAC ACGTCTCTCT CGGCTTATCC CCTGACACCG
TTAGCAGTAA GCTGAGTACA GATTAGGTTG TGCAGAGAGA GCCGAATAGG GGACTGTGGC

CCCGCCGACA GCCCGCATGG ACGAATCTAT CAATTCAGCC GCGGAGTCTA GTTTATATT
GGGCGGCTGT CGGGCGTACC TGCTTAGATA GTTAAGTCGG CGCCTCAGAT CAAATATAA

GCAGAATGCG AGATTGCTGG TTTATTATAA CAATATAAGT TTTCATTATT TTCAAAAAGG
CGTCTTACGC TCTAACGACC AAATAATATT GTTATATTCA AAAGTAATAA AAGTTTTCC

GGGATTTATT GTGGGTTTAG GTAAGAAATT GTCTAGTGCT CCTTTATGAG
CCCTAAATAA CACCCAAATC CATTCTTTAA CAGATCACGA GGAAATACTC

TTTAACCATC AGTCTGCCGG GTGTTCAGGC CGCTGAGAAT CCTCAGCTTA AAGAAAACCT
AAATTGGTAG TCAGACGGCC CACAAGTCCG GCGACTCTTA GGAGTCGAAT TTCTTTTGGA

GACGAATTTT GTACCGAAGC ATTCTTTTGGT GCAAGGGATC ATGAGCTACA ACTTGCTTGG
CTGCTTAAAA CATGGCTTCG TAAGAAACCA CGTTCCCTAG TACTCGATGT TGAACGAACC

ATTCCTACAA AGAAGCAGCA ATTTTCAGTG TCAGAAGCTC CTGTGGCAAT TGAATGGGAG
TAAGGATGTT TCTTCGTCGT TAAAAGTCAC AGTCTTCGAG GACACCGTTA ACTTACCCTC
```

(Continued on the next page)

FIG. 7B

```
GCTTGAATAC TTGCCTCAAG GACAGGATGA ACTTTGACAT CCCTGAGGAG ATTAAGCAGC
CGAACTTATG AACGGAGTTC CTGTCCTACT TGAAACTGTA GGGACTCCTC TAATTCGTCG

TGCAGCAGTT CCAGAAGGAG GACGCCGCAT TGACCATCTA TGAGATGCTC CAGAACATCT
ACGTCGTCAA GGTCTTCCTC CTGCGGCGTA ACTGGTAGAT ACTCTACGAG GTCTTGTAGA

TTGCTATTTT CAGACAAGAT TCATCTAGCA CTGGCTGGAA TGAGACTATT GTTGAGAACC
AACGATAAAA GTCTGTTCTA AGTAGATCGT GACCGACCTT ACTCTGATAA CAACTCTTGG

TCCTGGCTAA TGTCTATCAT CAGATAAACC ATCTGAAGAC AGTCCTGGAA GAAAAACTGG
AGGACCGATT ACAGATAGTA GTCTATTTGG TAGACTTCTG TCAGGACCTT CTTTTTGACC

AGAAAGAAGA TTTCACCAGG GGAAAACTCA TGAGCAGTCT GCACCTGAAA AGATATTATG
TCTTTCTTCT AAAGTGGTCC CCTTTTGAGT ACTCGTCAGA CGTGGACTTT TCTATAATAC

GGAGGATTCT GCATTACCTG AAGGCCAAGG AGTACAGTCA CTGTGCCTGG ACCATAGTCA
CCTCCTAAGA CGTAATGGAC TTCCGGTTCC TCATGTCAGT GACACGGACC TGGTATCAGT

GAGTGGAAAT CCTAAGGAAC TTTTACTTCA TTAACAGACT TACAGGTTAC CTCCGAAACT
CTCACCTTTA GGATTCCTTG AAAATGAAGT AATTGTCTGA ATGTCCAATG GAGGCTTTGA

GAAGATC
CTTCTAG
```

FIG.10A

```
              GATCTTAACA  TTTTCCCCT   ATCATTTTTC  CCGTCTTCAT  TTGTCATTTT
              CTAGAATTGT  AAAAAGGGGA  TAGTAAAAAG  GGCAGAAGTA  AACAGTAAAA

TTCCAGAAAA    AATCGTCATT  CGACTCATGT  CTAATCCAAC  ACGTCTCTCT  CGGCTTATCC
AAGGTCTTTT    TTAGCAGTAA  GCTGAGTACA  GATTAGGTTG  TGCAGAGAGA  GCCGAATAGG

CCTGACACCG    CCCGCCGACA  GCCCGCATGG  ACGAATCTAT  CAATTCAGCC  GCGGAGTCTA
GGACTGTGGC    GGGCGGCTGT  CGGGCGTACC  TGCTTAGATA  GTTAAGTCGG  CGCCTCAGAT

GTTTATATT     GCAGAATGCG  AGATTGCTGG  TTTATTATAA  CAATATAAGT  TTTCATTATT
CAAAATATAA    CGTCTTACGC  TCTAACGACC  AAATAATATT  GTTATATTCA  AAAGTAATAA

TTCAAAAAGG    GGGATTTATT  GTGGGTTTAG  GTAAGAAATT  GTCTAGTGCT  GTAGCCGCTT
AAGTTTTCC     CCCTAAATAA  CACCCAAATC  CATTCTTTAA  CAGATCACGA  CATCGGCGAA

CCTTTATGAG    TTTAACCATC  AGTCTGCCGG  GTGTTCAGGC  CGCTGAGAAT  CCTCAGCTTA
GGAAATACTC    AAATTGGTAG  TCAGACGGCC  CACAAGTCCG  GCGACTCTTA  GGAGTCGAAT

AAGAAAACCT    GACGAATTTT  GTACCGAAGC  ATTCTTTGGT  GCAAGGGATC  AATTCTATGT
TTCTTTTGGA    CTGCTTAAAA  CATGGCTTCG  TAAGAAACCA  CGTTCCCTAG  TTAAGATACA

TCCCAACCAT    TCCCTTATCC  AGGCTTTTTG  ACAACGCTAG  TCTCCCGCC   CATCGTCTGC
AGGGTTGGTA    AGGGAATAGG  TCCGAAAAAC  TGTTGCGATC  AGAGGCGCGG  GTAGCAGACG
```

(Continued on the next page)

FIG. 10B

```
ACCAGCTGGC CTTTGACACC TACCAGGAGT TTGAAGAAGC CTATATCCCA AAGGAACAGA
TGGTCGACCG GAAACTGTGG ATGGTCCTGA AACTTCTTCG GATATAGGGT TTCCTTGTCT

AGTATTCATT CCTGCAGAAC CCCCAGACCT CCCTCTGTTT CTCAGAGTCT ATTCCGACAC
TCATAAGTAA GGACGTCTTG GGGGTCTGGA GGGAGACAAA GAGTCTCAGA TAAGGCTGTG

CCTCCAACAG GGAGGAAACA CAACAGAAAT CCAACCTAGA GCTGCTCCGC ATCTCCCTGC
GGAGGTTGTC CCTCCTTTGT GTTGTCTTTA GGTTGGATCT CGACGAGGCG TAGAGGACG

TGCTCATCCA GTCGTGGCTG GAGCCCGTGC AGTTCCTCAG GAGTGTCTTC GCCAACAGCC
ACGAGTAGGT CAGCACCGAC CTCGGGCACG TCAAGGAGTC CTCACAGAAG CGGTTGTCGG

TGGTGTACGG CGCCCTCTGAC AGCAACGTCT ATGACCTCCT AAAGGACCTA GAGGAAGGCA
ACCACATGCC GCGGAGACTG TCGTTGCAGA TACTGGAGGA TTTCCTGGAT CTCCTTCCGT

TCCAAACGCT GATGGGGAGG CTGGAAGATG GCAGCCCCCG GACTGGGCAG ATCTTCAAGC
AGGTTTGCGA CTACCCCTCC GACCTTCTAC CGTCGGGGGC CTGACCCGTC TAGAAGTTCG

AGACCTACAG CAAGTTCGAC ACAAACTCAC ACAACGATGA CGCACTACTC AAGAACTACG
TCTGGATGTC GTTCAAGCTG TGTTTGAGTG TGTTGCTACT GCGTGATGAG TTCTTGATGC

GGCTGCTCTA CTGCTTCAGG AAGGACATGG ACAAGGTCGA GACATTCCTG CGCATCGTGC
CCGACGAGAT GACGAAGTCC TTCCTGTACC TGTTCCAGCT CTGTAAGGAC GCGTAGCACG

AGTGCCGCTC TGTGGAGGGC AGCTGTGGCT TCTAG
TCACGGCGAG ACACCTCCCG TCGACACCGA AGATC
```

DNA SEQUENCE INVOLVED IN GENE EXPRESSION AND PROTEIN SECRETION, EXPRESSION-SECRETION VECTOR INCLUDING THE DNA SEQUENCE AND THE METHOD OF PRODUCING PROTEINS BY USING THE EXPRESSION-SECRETION VECTOR

BACKGROUND OF THE INVENTION

1. Field of the Invention

This invention relates to a DNA sequence which comprises a DNA fragment consisting of a region involved in the expression of a gene coding for an extracellular enzyme of a bacterium of the genus Bacillus and a region involved in the expression of the enzyme thus expressed and, if necessary, a DNA segment joined to said DNA sequence on its downstream side which includes a restriction endonuclease cleavage site or sites capable of joining thereto a DNA fragment containing a gene coding for a desired protein; an expression-secretion vector formed by joining the DNA sequence to a plasmid DNA or phage DNA capable of replicating in a host bacterium of the genus Bacillus; and a method of producting proteins by use of said vector.

2. Description of the Prior Art

The marked development of molecular biology in recent years has made it possible to produce and secrete a desired protein from a host microorganism by joining a gene coding for a desired protein to a proper vector and introducing the resulting recombinant DNA into a host microorganism.

As the host microorganism, *Escherichia coli* has been so far used which is most advanced in genetical and molecular-biological investigations. However, when *Escherichia coli* is used as the host bacterium, the desired protein is usually accumulated within the cells, thus making it very difficult to purify the desired protein. Furthermore, the desired protein, though purified, is unavoidably contaminated with pyrogens, raising a serious problem.

On the other hand, bacteria of the genus Bacillus have characteristics of extracellular secretion of a large amount of protein, lack pathogenicity and have long been used in the fermentation industry. Since their safety is thus established, they have been regarded as important as the host bacteria capable of solving the aforesaid problems involved in the separation and purification of proteins from the interior of the cells. Accordingly, it would be of great industrial significance from the viewpoint of microbial production of proteins to create an expression-secretion vector suitable for use in bacteria of the genus Bacillus.

From this point of view, attempts have been made to develop expression-secretion vectors capable of utilizing bacteria of the genus Bacillus as the host. Further, there is an increasing demand for expression-secretion vectors which permit an extracellular production of a desired protein in large amounts.

SUMMARY OF THE INVENTION

The neutral protease of *Bacillus amyloliquefaciens* is a protein secreted in large amounts within a short period of time by the bacterium. The neutral protease gene of the bacterium has been already cloned in a host bacterium of the genus Bacillus and the entire DNA sequence of the neutral protease gene containing the promoter region involved in its expression and the region involved in the secretion of the neutral protease thus expressed has been elucidated. (The entire DNA sequence is described in U.S. patent application Ser. No. 686,892.)

Moreover, it has been found that there is an open reading frame, which comprises 663 base pairs and which contains a DNA sequence coding for the prepropeptide comprising 221 amino acids, on the upstream side of the DNA sequence coding for the mature neutral protease in neutral protease gene.

In view of the importance of the expression-secretion vector capable of utilizing bacteria of the genus Bacillus as the host as described above, the present inventors have made extensive investigations on this subject matter. In the process of the investigations, they have marked the neutral protease of *B. amyloliquefaciens* as described above and then arrived at the thought that the prepro-peptide was split off during the process of secretion and played an important role in the secretion of the neutral protease based on the fact that the mature neutral protease was synthesized within the cell in the form joined to the prepropeptide but none of the prepro-peptide was present in the extracellularly secreted mature neutral protease.

The present inventors have then made further detailed investigations on the structure of the prepropeptide and the DNA sequence coding therefor. As a result, a difference was noted between this prepropeptide and the signal-peptide of extracellular enzyme conventionally known in the art, i.e., the polypeptide comprising 20–40 amino acids, synthesized in the form joined to the upstream side of the N-terminus of mature protein within the cell of a bacterium, playing an important role in its passage through the cell membrane during the process of secretion. In addition, it has been newly founded that a deletion in a suitable length occurring in the prepro-peptide coding region can enhance the extracellular production of a desired protein dependent on the deleted prepropeptide higher than that dependent on the signal-peptide or the entire prepro-peptide. The present invention has been completed on the basis of this discovery.

Thus, the object of the present invention is to provide a DNA sequence capable of utilizing a bacterium of the genus Bacillus as the host and permitting the extracellular production of a desired protein in large amounts by a host bacterium, and an expression-secretion vector incorporated with the DNA sequence.

The DNA sequence involved in the expression of a gene and the secretion of the resulting protein according to the present invention can be prepared by subjecting a DNA sequence consisting of a region involved in the expression of an extracellular enzyme gene and the secretion of the enzyme thus expressed to a deletion in the region involved in the secretion that can enhance its function for extracellular production of a desired protein by a host bacterium. No techniques have been present to enhance the function of a DNA sequence involved in the expression of a gene and the secretion of the resulting protein by the deletion until the present inventors now disclose this invention.

Thus, a desired protein can be obtained by joining a gene coding for the desired protein to the expression-secretion vector of the present invention, which contains the DNA sequence enhanced in the function of the expression of the gene and the secretion of the resulting protein by the deletion as described above, so as to form a recombinant DNA molecule; introducing the recombinant DNA molecule into a bacterium of the genus Bacillus; culturing the resulting transformed bacterium so as to cause the desired protein to be secreted in large amounts into its culture medium; and then recovering the protein from the supernatant of the culture medium and purifying it according to a simple procedure.

Consequently, use of the expression-secretion vector of the present invention makes it possible to solve the aforesaid problems raised upon using *Escherichia coli* as the host and to produce a highly-secured protein in a high efficiency.

For instance, production of human growth hormone, which is physiologically active in auxetic effects, protein assimilation, lipometabolism and sugar metabolism, has conventionally been effected by the method in which a hypohysis extracted from the human remains is used as a raw material. This method, however, is very poorly productive and has thus failed to supply the demand to a sufficient degree because of the complex process required in the separation and extraction of the product from the raw material in addition to the difficulty in the access to the raw material. Moreover, death of patients administered with the human growth hormone due to the inclusion of virus in it has been pointed out as a serious problem attended by the production of human growth hormone from the human remains.

Attempts have been made to produce human growth hormone by means of the recombinant DNA technology using *Escherichia coli* as the host bacterium. In this case, however, the human growth hormone is accumulated within the cells of *Escherichia coli* as described above, thus making it very difficult to purify the human growth hormone. Further, the hormone is unavoidably contaminated with pyrogens, raising a large problem. Moreover, the human growth hormone produced in *Escherichia coli* is a methionyl human growth hormone formed by adding methionine to the N-terminus of the natural human growth hormone and its structure is, therefore, different from the natural human growth hormone. The methionyl human growth hormone involves such a problem as to increases of the level of anti-hGH antibody in the blood of a patient administered with it. Thus, it has been anticipated to establish a method for producing human growth hormone devoid of methionine residue by means of the recombinant DNA technology.

The expression-secretion vector of the present invention can meet the foregoing anticipation satisfactorily and thus makes it possible to produce a highly-secured human growth hormone in a good productivity by such simple process steps as those of joining a gene coding for human growth hormone to said vector to form a recombinant DNA molecule, transforming a bacterium of the genus Bacillus with the recombinant DNA molecule, culturing the transformed bacterium in a culture medium and separating and purifying the human growth hormone secreted in large amounts into the culture medium.

BRIEF DESCRIPTION OF THE DRAWINGS

FIG. 1 is a drawing illustrating the nucleotide sequence of the DNA fragment involved in the expression of a gene and the secretion of the protein thus expressed in pNPA 84 DNA;

FIG. 2 is a drawing illustrating the nucleotide sequence of the DNA segment containing restriction endonuclease cleavage sites capable of joining thereto a gene coding for a desired protein;

FIG. 3 is a drawing illustrating the nucleotide sequence of the DNA comprising the DNA fragment involved in the expression of a gene and the secretion of the protein thus expressed and the DNA segment which is located on the downstream side thereof and which contains a restriction endonuclease cleavage site capable of joining thereto a DNA fragment comprising a gene coding for a desired protein in the expression-secretion vector pES 84;

FIG. 7 (parts A and B) illustrates the nucleotide sequence of the DNA containing the promoter region and the neutral protease prepro-peptide coding region having a deletion and the mature human interferon-β gene in the recombinant DNA molecule pESI84;

FIG. 10 (parts A and B) is a drawing illustrating the nucleotide sequence of the DNA containing the promoter region, deleted prepro-peptide coding region and the mature human growth hormone gene in the recombinant DNA molecule phGH 928.

In FIGS. 4, 5, 6, 8, 9 and 11, 1 represents the region involved in the expression of a neutral protease gene;

Figure 4:
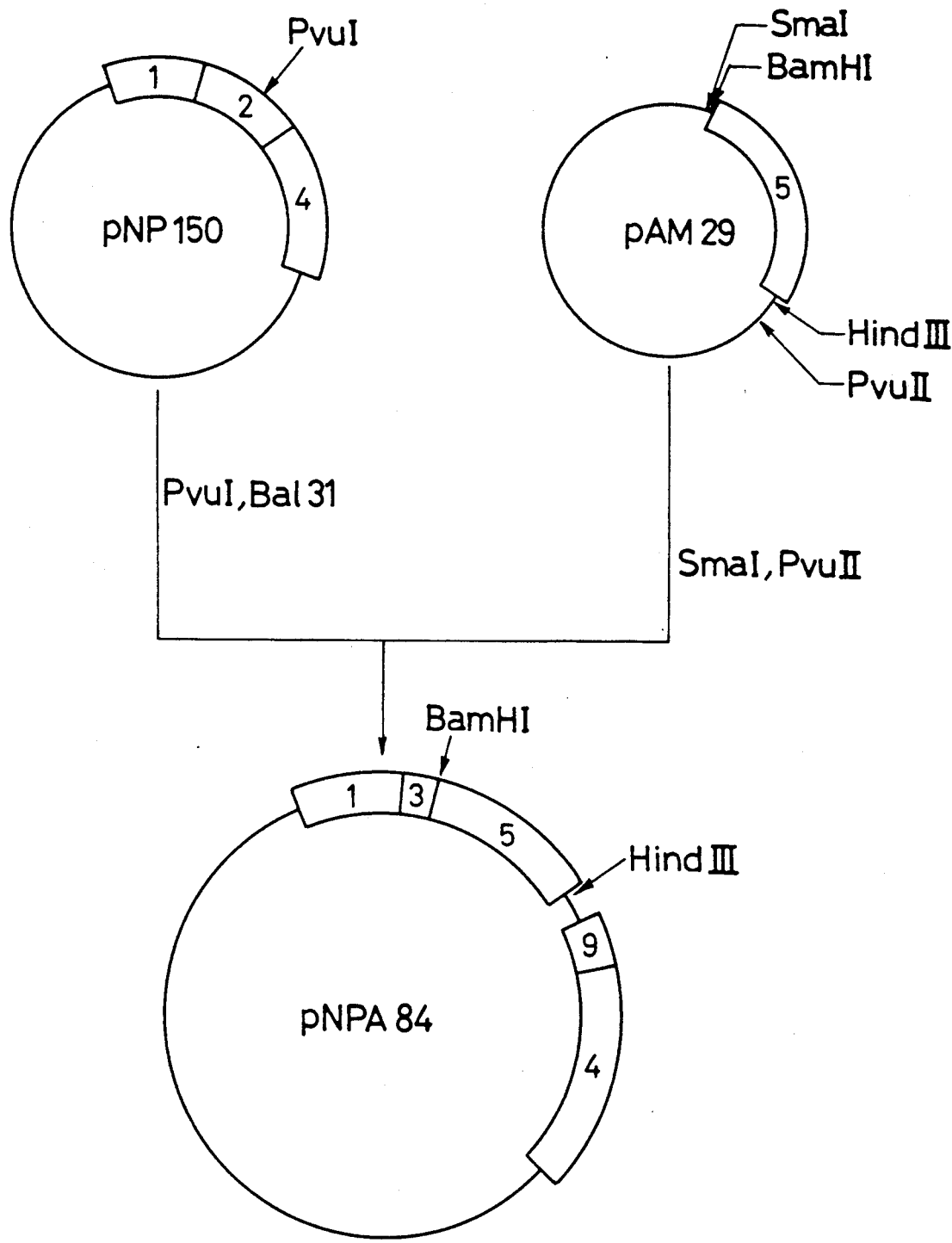
FIG. 4 is a drawing illustrating the procedure for the preparation of a recombinant DNA molecule which contains the neutral protease prepro-peptide coding region having various length of deletion and joining thereto the mature α-amylase gene devoid of its signal-peptide coding region.

2 represents the DNA fragment coding for the entire prepro-peptide of neutral protease;

3 represents the region involved in the secretion of protein contained in the expression-secretion vectors pNPA 84 and pES 84;

4 represents the DNA sequence coding for mature neutral protease;

5 represents the DNA sequence containing the mature α-amylase gene devoid of its signal-peptide coding region;

6 represents the mature human interferon-β gene devoid of its signal-peptide coding region;

7 represents the mature human growth hormone gene devoid of its signal-peptide coding region;

8 represents a DNA segment containing a restriction endonuclease cleavage site or sites; and 9 represents a residual DNA fragment derived from DNA fragment 2.

DETAILED DESCRIPTION OF THE INVENTION AND PREFERRED EMBODIMENTS

The DNA sequence involved in the expression of a gene as described herein includes the promoter region containing the -35 and -10 regions, which are the sites for recognition and binding of RNA polymerase, and the ribosome binding region by which the messenger RNA synthesized by the RNA polymerase can bind rebosomes. These regions play an important role in the expression of a gene, and the structure of the regions is directly associated with the level of expression.

The RNA polymerases and ribosomes of Bacillus bacteria have strict specificity in the recognition of the promoter region and the ribosome binding region. In order to express a gene coding for a desired protein in a bacterium of the genus Bacillus used as the host, these regions involved in the expression of the gene in the present invention should preferably originate from a bacterium of the genus Bacillus.

As the substance involved in the secretion of the protein produced in a cell as a result of gene expression from the inside to the outside of the cells, a polypeptide, called "a signal-peptide" located upstream from the mature protein present outside the cells is known to be essential. It has been demonstrated that this polypeptide is synthesized within the cells in the form joined to the upstream side of the N-terminus of the mature protein and, during the secretion of the mature protein, plays an important role in its passage through the cell membrane.

Further, it is very important from a practical point of view in the creation of the expression-secretion vector to use a gene coding for an extracellular enzyme which can be produced and extracellularly secreted in large amounts within a short period of time for the purpose of an extracellular production of a desired protein in a high level.

From the above point of view, the DNA sequence involved in the expression of a gene and the secretion of the resulting protein according to the present invention may preferably be derived from the gene coding for an extracellular enzyme contained in a bacterium of the genus Bacillus which produces and secretes the enzyme. These enzymes may include, for example, extracellular protease, α-amylase and levansucrase. Among others, the neutral protease of *Bacillus amyloliquefaciens* is preferred due to the production and secretion in large amounts within a short period of time by Bacillus bacteria.

The DNA sequence involved in the expression of a gene and the secretion of the protein thus produced according to the present invention can be prepared by isolating a DNA sequence involved in the expression of the gene and the secretion of the enzyme thus expressed from a gene coding for the aforesaid extracellular enzyme and subjecting the isolated DNA sequence to a deletion in the DNA sequence involved in the secretion of the enzyme in such a way that the extracellular production of a desired protein can be enhanced by using the DNA sequence incorporated in a recombinant DNA molecule as described below.

Although various procedures of genetic engineering can be applied to each of the steps to obtain the DNA sequence of the present invention, the method established by the present inventors as exemplified in Example 1 described below is useful.

The expression-secretion vector of the present invention is a combination comprising the aforesaid DNA sequence involved in the expression of a gene and the secretion of the protein thus expressed and a DNA fragment derived from a phage DNA or a plasmid DNA that is capable of replication in a bacterium of the genus Bacillus with the help of a DNA sequence containing an appropriate restriction endonuclease cleavage site or sites. By joining a DNA fragment containing a gene coding for a desired protein to the aforesaid expression-secretion vector, it becomes possible to effect the production and extracellular secretion of the desired protein. More specifically, this can be accomplished by joining a DNA fragment containing a gene coding for a desired protein to the aforesaid expression-secretion vector on the downstream side of the DNA sequence involved in the expression of a gene and the secretion of the protein thus expressed introducing the resulting recombinant DNA molecule into the host microorganism, i.e., a bacterium of the genus Bacillus; culturing the host microorganism so as to cause the gene coding for the desired protein to be expressed in the host microorganism and also cause the protein thus produced to be secreted in large amounts into the culture medium of the host microorganism; and then recovering the protein from the supernatant of the culture medium and purifying it according to a simple procedure.

As plasmids or phages which form the expression-secretion vector, there may be used any plasmids or phages that are capable of replicating in Bacillus bacteria. As a plasmid that is being commonly used may be mentioned pUB110 which is derived from Staphylococcus.

The DNA segment containing one or more restriction endonuclease cleavage sites may favorably be joined to the aforesaid DNA sequence on its downstream side from the standpoint of joining thereto a DNA fragment containing a gene coding for a desired protein. Any DNA sequences may be available so far as they are capable of joining thereto a DNA fragment coding for a desired protein. For example, it is useful to employ the DNA sequence consisting of 7 bp present at the end of the DNA sequence shown in FIG. 3, which used in the examples described below.

As an example of its application, the present inventors practically succeeded in producing and secreting human interferon-β and human growth hormone into a culture medium in a large amount for the first time in the world by using pES84 as one of the expression-secretion vectors of the present invention and *Bacillus subtilis* as the host microorganism (Examples 3, 4 and 5).

It was confirmed from this fact that the DNA sequence of the present invention typified by the DNA sequence containing the region involved in the expression of a neutral protease gene and the secretion of the protein thus expressed comprised in pES84 was markedly effective for the expression of a gene coding for a desired protein and the secretion of the protein thus expressed.

As described in the above, the present inventors succeeded in the expression of a gene coding for a foreign protein and the secretion of the protein thus expressed to the outside of the cells. This has also made it possible to extracellularly produce a desired protein, for example, interferon, growth hormone, interleukin, nerve growth factor, kallikrein, plasminogen activator and other physiologically active polypeptides or enzymes by joining or inserting, to a restriction endonuclease cleavage site or sites present in the expression-secretion vector (as shown in FIG. 3) of the present invention, a DNA fragment containing a desired gene, i.e., a gene coding for one of the above-described proteins, either directly or with the aid of a suitable linker, and transforming *Bacillus subtilis* by using the resulting recombinant DNA molecule, thereby causing the extracellular production of the desired protein in large amounts.

The method of creating the expression-secretion vector (pES84) of the present invention, and the expression of a human interferon-β gene and human growth hormone gene and the secretion of the human interferon-β and human growth hormone thus produced are described with reference to the following examples. However, these examples are not to be construed to limit the scope of the present invention.

EXAMPLE 1

Method of creating DNA fragments, each of which has various length of deletion in the prepropeptide coding region A mixture of DNA fragments, each of which contains a region involved in the expression of the neutral protease gene and a prepro-peptide coding region having a deletion in various length was prepared from plasmid pNP150 consisting of a neutral protease gene derived from Bacillus amyloliquefaciens and plasmid pUB110 DNA by the following procedure using an exonuclease (Bal31):

Plasmid pNP150 DNA was first prepared from Bacillus subtilis strain MT-0150 carrying the plasmid according to the method of Gryczan [Gryczan, T. J. et al., J. Bacteriol 134, 318 (1978)]. A stock of the B. subtilis strain MT-0150 was deposited on Dec. 10, 1983 under deposition No. FERM-BP-425 in accordance with the Budapest Treaty with the Fermentation Research Institute (FRI) of the Agency of Industrial Science and Technology, 1-1-3, Higashi 1-chome, Yatabe-Machi, Tsukuba-gun, Ibaraki-ken 305, Japan.

10 μg of the plasmid pNP150 DNA thus obtained was treated at 37° C. with 10 units of the restriction endonuclease PvuI (Boehringer Mannheim A.G.) for 1 hour, thereby cleaving the plasmid completely. The resulting PvuI-cleaved DNA was extracted three times with phenol, extracted with ether to remove any remaining phenol, and then recovered by precipitation with ethanol.

Subsequently, the recovered DNA was treated at 30° C. with 10 units of exonuclease Bal31 (Boehringer Mannheim A.G.) for 50 minutes.

In addition to the DNA and the exonuclease, the reaction system contained 1 mM EDTA, 12 mM $CaCl_2$, 12 mM $MgCl_2$ and 600 mM NaCl in a 20 mM Tris-HCl buffer solution (pH 8.1).

After completion of the reaction, the DNA was purified by extraction with phenol and extraction with ether, and then recovered by precipitation with ethanol. The recovered DNA (hereinafter referred to as the exonulease-treated DNA) was dissolved in 50 μl of a 50 mM Tris-HCl buffer solution (pH 7.5) (hereinafter referred to as DNA buffer). The DNA concentration in the solution was 0.1 μg/μl. DNA fragments, each of which contains the DNA sequence comprising a region involved in the expression of the neutral protease gene and a prepro-peptide coding region having a deletion in various length were obtained in accordance with the above procedure.

The extracellular production of α-amylase dependent on each of various lengths of the prepro-peptide coding regions contained in the resulting DNA fragments was determined in the following manner:

A DNA sequence containing the mature α-amylase gene devoid of its signal-peptide coding region (hereinafter referred to as the mature α-amylase gene) was first prepared from plasmid pAM29 which contained said gene.

This plasmid pAM29 was prepared using a synthetic DNA in such a way that the DNA sequence containing the mature α-amylase gene holds cleavage sites for the restriction endonucleases SmaI and BamHI on its N-terminus and cleavage sites for the restriction endonucleases HindIII and PvuII on its C-terminus.

The plasmid pAM29 (10 μg) was digested with 10 units of the restriction endonuclease SmaI (Takara Shuzo Co.) and 10 units of the restriction endonuclease PvuII (Takara Shuzo Co.). Thereafter, 3 μg of a DNA fragment containing the mature α-amylase gene comprising 1700 base pairs were prepared from the mixture of the resulting digested products by 1% agarose gel electrophoresis.

In the resulting DNA fragment, a mature α-amylase gene was located between a DNA sequence containing a cleavage site for restriction endonuclease BamHI on its N-terminus and a DNA sequence containing a cleavage site for restriction endonuclease HindIII on its C-terminus.

This DNA fragment was dissolved in 30 μl of the DNA buffer. Then, a recombinant DNA molecule was prepared by joining the resulting DNA fragment to the aforementioned digested pNP150 having a deletion in various length in accordance with the procedure shown in FIG. 4.

Specifically, 10 μl of the above DNA buffer in which the DNA fragment containing the mature α-amylase gene was dissolved and 10 μl of the exonuclease-treated DNA solution were reacted at 10° C. for 18 hours using 10 units of the $T_4$ ligase of Escherichia coli (Takara Shuzo Co.) to produce a recombinant DNA molecule. In addition to the DNAs and the ligase, the reaction system contained 6.5 mM $MgCl_2$, 10 mM dithiothreitol and 2 mM ATP (adenosine triphosphate) in a 66 mM Tris-HCl buffer solution (pH 7.5).

Using this recombinant DNA molecule, Bacillus subtilis was transformed according to the protoplast method (Chang, S. and Cohen, S. N., Mol. Gen. Genet., 168 111 (1978)]. To the regeneration medium of the protoplasts were added 100 μl/ml of kanamycin sulfate (Boehringer Mannheim A.G.) and soluble starch at a final concentration of 1%. As the host for transformation, Bacillus subtilis strain 1A289 lacking the ability to produce amylase (a stock strain maintained in the Bacillus Genetic Stock Center, the Ohio State University, Department of Microbiology, 484 West 12th Avenue, Columbus, Ohio 43210, U.S.A.) was used. Transformants producing and secreting amylase were selected according to the iodine/potassium iodide method [J. Bacteriol., 119, 416 (1974)]. As a result, 78 transformed strains producing and secreting amylase were obtained.

These transformed strains were shake cultured in the BY medium (0.5% meat extract, 0.2% yeast extract, 0.2% NaCl, 1% polypeptone and 5 μg/ml kanamycin) at 37° C. for 10 hours and the cells were separated from the supernatant of the medium by centrifugation. Then, the supernatant of the culture medium was assayed for α-amylase activity by examining the formation of reducing groups from soluble starch with the aid of dinitrosalcylic acid (Biochemical Information II, p. 28–30 catalogue of Boehringer Mannheim A.G.). An example of the results obtained is shown in Table 1.

The transformant B. subtilis strain 207-25 (pPA33) mentioned in Table 1 was formed by transforming B. subtilis strain 1A289 with a recombinant DNA molecule obtaining by deleting the DNA sequence coding for the mature neutral protease from the plasmid pNP150 used in this example and inserting the mature α-amylase gene derived from plasmid pAM29 used in this example into the part of the plasmid pNP150, in which the DNA sequence coding for the mature neutral protease had been previously located. Therefore, the extracellular production by this transformant depended on the DNA sequence coding for the entire prepropeptide of the neutral protease contained in plasmid pPA33. In addition, the detailed information relating to its construction and preparation method is described in U.S. patent application Ser. No. 818,745.

TABLE 1

Accumulation of α-amylase by transformants in culture medium

| Transformant | length of prepro-peptide coding region (bp) | Amylase activity (U/ml) |
| --- | --- | --- |
| B. subtilis | | |
| 207-25 (pNPA105) | 130 | 3.5 |
| (pNPA84) | 150 | 7.1 |
| (pNPA58) | 170 | 6.0 |
| (pNPA86) | 190 | 6.8 |
| (pNPA73) | 230 | 0.5 |
| (pNPA152) | 240 | 5.3 |
| (pNPA71) | 250 | 0.1 |
| (pNPA107) | 260 | 0.5 |
| (pNPA133) | 260 | 1.7 |
| (pNPA155) | 270 | 0.1 |
| (pNPA108) | 300 | 2.5 |
| (pNPA85) | 340 | 2.8 |
| (pNPA74) | 350 | 5.5 |
| (pPA33) | 660 | 4.8 |

Thus, a transformant (#84) which secretes α-amylase to the outside of the cells in the largest amount (about 300 times those of wild strains) was selected among the resulting transformed strains.

A plasmid (pNPA84) was prepared from the transformant (#84) according to the alkaline method [Birnboim, H.C. et al., Nucleic Acids Res. 7 1513 (1979)]. The nucleotide sequence of the plasmid (pNPA84) was determined according to the Maxam-Gilbert method [Maxam, A. M. & Gilbert, W. Proc. Natl. Acad. Sci. USA 74 560 (1977)]. As a result, it was found that pNPA84 is a plasmid formed by joining the mature α-amylase gene to the DNA fragment containing the DNA sequence shown in FIG. 1 on its downstream side. In addition it was confirmed that the junction region of them has the following nucleotide sequence:

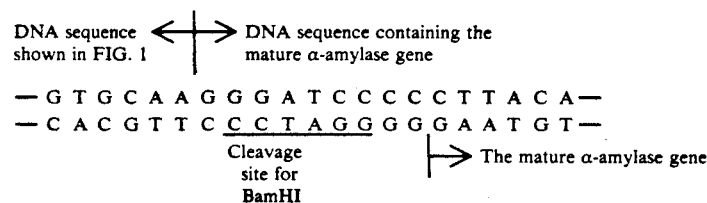

As can be seen from the above results, the extracellular production of α-amylase in a large amount could be realized by using the DNA fragment containing the DNA sequence shown in FIG. 1.

EXAMPLE 2

Construction of an expression-secretion vector pES84

As a result of Example 1, it was found that the DNA sequence shown in FIG. 1 has an effect on the extracellular production of a protein corresponding to a inserted foreign gene in a recombinant DNA molecule. Then, an expression-secretion vector containing this DNA sequence and the restriction sites, i.e. the expression-secretion vector pES84 was constructed, in which a DNA segment containing a restriction endonuclease cleavage site or sites capable of joining thereto a gene coding for a desired protein was joined to the region involved in the expression of a neutral protease gene and the secretion of the protein thus expressed on the downstream side thereof. The method for creating the vector pES84 is described as follows (see FIG. 5):

Preparation of the region involved in the expression of a neutral protease gene and the secretion of the protein thus expressed was effected first by preparing 2 μg of the plasmid pNPA84 carrying a DNA sequence containing the DNA fragment shown in FIG. 1 from the transformant (#84) obtained in Example 1 according to the alkaline method [Birnboim, H. C. et al., Nucleic Acids Res. 7 1513 (1979)]. The DNA was dissolved in 10 μl of the DNA buffer. Then, 10 μl of the solution was treated with the endonucleases BamHI (Takara Shuzo Co.) and HindIII (Takara Shuzo Co.). Thereafter, 0.2 μg of a DNA fragment comprising pNPA84 but deprived of the mature α-amylase gene (hereinafter referred to as DNA fragment A) was prepared by agarose gel electrophresis and dissolved in 2 μl of the DNA buffer.

Separately, a DNA fragment available for construction of a DNA sequence containing a restriction endonuclease cleavage site capable of joining thereto a DNA fragment containing a gene coding for a desired protein on the downstream side of the DNA fragment shown in FIG. 1 was synthesized chemically. Specifically, the both strands of the DNA sequence shown in FIG. 2 were chemically synthesized and purified separately according to the method of Otsuka [Eiko Otsuka, Kagaku no Ryoiki (Field of Chemistry) 35 (10) 762 (1981)] and 1 μg each of the resulting synthesized DNAs was dissolved in 10 μl of the DNA buffer. Then, the both single-stranded DNAs were reconstructed to form a double-stranded DNA containing the DNA sequence shown in FIG. 2. The reconstruction was carried out by mixing 5 μl each of the solutions, each of which contains either of the single-stranded DNAs, treating the resulting mixture at 90° C. for 5 minutes and allowing it to stand at 0° C. for one hour.

Figure 5:
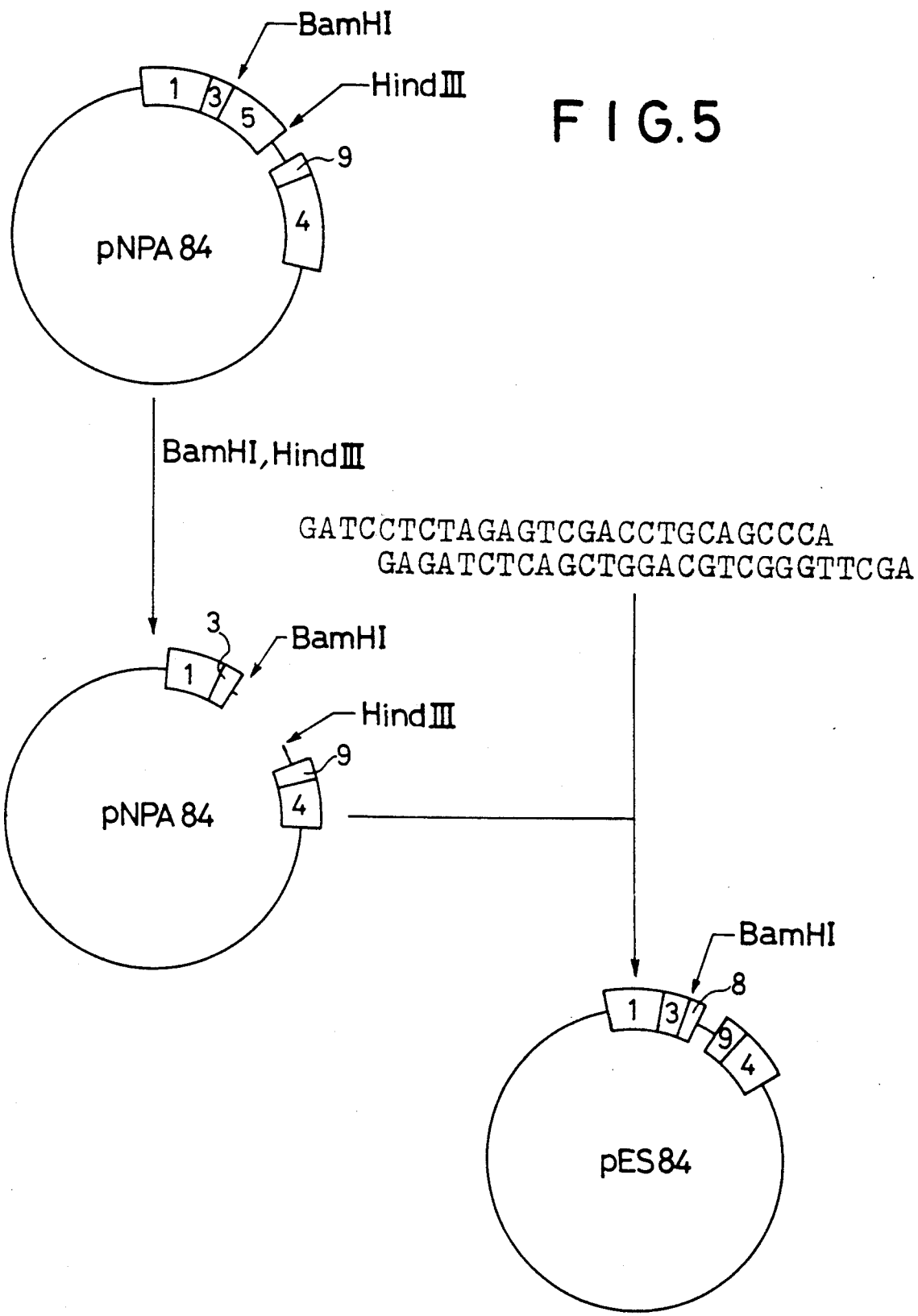
FIG. 5 is a drawing illustrating the procedure for creating the expression-secretion vector pES 84.

The double-stranded DNA thus reconstructed and the previously obtained DNA fragment A were joined together as shown in FIG. 5 to form the expression-secretion vector pES84.

Specifically, 10 μl of the solution containing the aforesaid double-stranded DNA and 2 μl of the solution containing the DNA fragment A were reacted at 4° C. for 16 hours using the T4 DNA ligase of Escherichia coli (Takara Shuzo Co.) to prepare a recombinant DNA molecule comprising the synthesized double-stranded DNA and the DNA fragment A. In addition to the DNAs and the ligase, the reaction system contained 6.6 mM MgCl₂, 10 mM dithiothreitol and 2 mM ATP (adenosine triphosphate) in a 66 mM Tris-HCl buffer solution (pH 7.5). *Bacillus subtilis* was transformed using the recombinant DNA molecule in accordance with the protoplast method (stated above) and a plasmid was obtained from the transformant according to the alkaline method (stated above). The nucleotide sequence of the plasmid was determined in accordance with the Maxam-Gilbert method (stated above).

As a result, it was confirmed that the resulting plasmid contained the DNA sequence shown in FIG. 3, in which a DNA segment containing a restriction endonuclease cleavage site capable of joining thereto a gene coding for a desired protein was joined to the DNA sequence shown in FIG. 1 on the downstream side thereof. The plasmid (pES84) thus obtained was then introduced into *Bacillus subtilis* strain MT-0207 (A stock of this strain was deposited on Oct. 14, 1985 under deposition No. FERM-BP-926 in accordance with the Budapest Treaty with FRI mentioned above) in accordance with the protoplast method (stated above), thereby obtaining a transformant(*Bacillus subtilis* strain MT-8400, A stock of this strain was deposited on Oct. 14, 1985 under deposition No. FERM-BP-923 in accordance with the Budapest Treaty with FRI) containing the expression-secretion vector pES84.

EXAMPLE 3

Expression of a human interferon-β gene in *Bacillus subtilis* and secretion of human interferon-β using the expression-secretion vector pES84

A human interferon-β gene was prepared from plasmid pIF20 containing its structure gene. Specifically, the plasmid pIF20 was constructed using a synthetic DNA in such a way that each of the ends of the DNA sequence coding for the mature protein deprived of the signal-peptide coding region involved in the secretion of human interferon-β has a restriction endonuclease Sau3AI cleavage site. The plasmid pIF20 was cleaved with the restriction endonuclease Sau3AI (Takara Shuzo Co.) to obtain a DNA sequence of about 500 base pairs coding for the mature protein deprived of the signal-peptide coding region of human interferon-β (hereinafter referred to as the mature human interferon-β gene).

Figure 6:
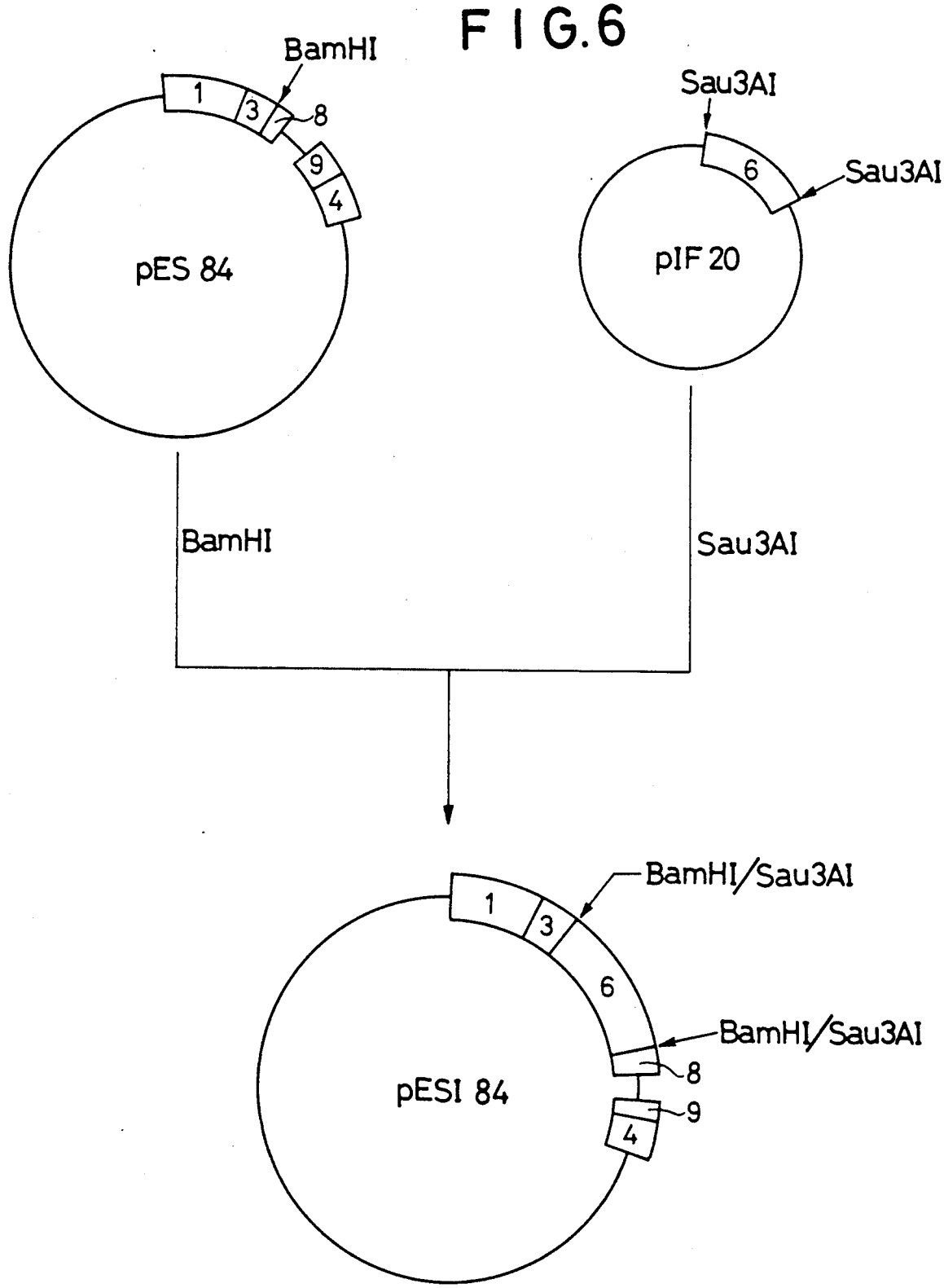
FIG. 6 is a drawing illustrating the procedure for creating the recombinant DNA molecule pESI 84.

The mature human interferon-β gene (0.1 μg) and the expression-secretion vector pES84 (0.1 μg) which had been cleaved completely with the restriction endonuclease BamHI (Takara Shuzo Co.) were reacted using 10 units of the $T_4$ DNA ligase of *Escherichia coli* (Takara Shuzo Co.) to form a recombinant DNA molecule (see FIG. 6; the reaction conditions and the composition of the reaction system were the same as those used in joining the fragment A and the double-stranded DNA in Example 2). Using the recombinant DNA molecule thus obtained, *Bacillus subtilis* strain MT-0207 was transformed according to the protoplast method (stated above) to obtain a transformant. The transformant was shake cultured at 30° C. for 14 hours in the Penassay medium (Difco). Thereafter, the culture medium was centrifuged to separate the cells from the supernatant of the culture medium. The assay for the immunoactivity of the human interferon-β contained in the supernatant of the culture medium was made by the enzyme-immunoassay method using an antiserum against human interferon-β [Eiji Ishikawa (ed.), Enzyme-immunoassay, p. 67 (1981)]. As a result, $2.5 \times 10^4$ U/ml of human interferon-β was found to be present in the supernatant of the culture medium of the transformant. The plasmid (pESI84) to be contained in the transformed strain (*Bacillus subtilis* strain MT-8401, a stock of this strain was deposited on Oct. 14, 1985 under deposition No. FERM-BP-924 in accordance with the Budapest Treaty with FRI mentioned above ) producing and secreting human interferon-β was prepared according to the alkaline method (stated above). Further, the DNA sequence in the promoter and prepro-peptide coding regions derived from the neutral protease gene and the region of the mature human interferon-β gene in the plasmid (pESI84) was determined according to the Maxam-Gilbert method (FIG. 7). As a result, it was confirmed that the plasmid (pESI84) is a recombinant DNA molecule comprising the expression-secretion vector pES84 of the present invention and the mature human interferon-β gene.

One U unit used herein corresponds to $1 \times 10^{-8}$ mg of human interferon-β.

Conventionally, human interferon-β has been obtained with a great deal of effort from human tissues or cultured cells originating from human tissues. By using *Bacillus subtilis* strain (MT-8401) transformed with the recombinant DNA molecule (pESI84) according to the present invention, it has become possible to obtain human interferon-β with ease and in large amounts.

EXAMPLE 4

Expression of a human growth hormone gene in *Bacillus subtilis* and secretion of human growth hormone using the expression-secretion vector pES84

A human growth hormone gene was prepared using a plasmid phGH318 containing said gene in the following manner:

The plasmid phGH318 was cleaved with the restriction endonucleases BamHI (Takara Shuzo Co.) and HindIII (Takara Shuzo Co.) to prepare a DNA fragment containing the DNA sequence comprising about 900 base pairs and coding for human growth hormone (hereinafter referred to as DNA fragment B).

Figure 8:
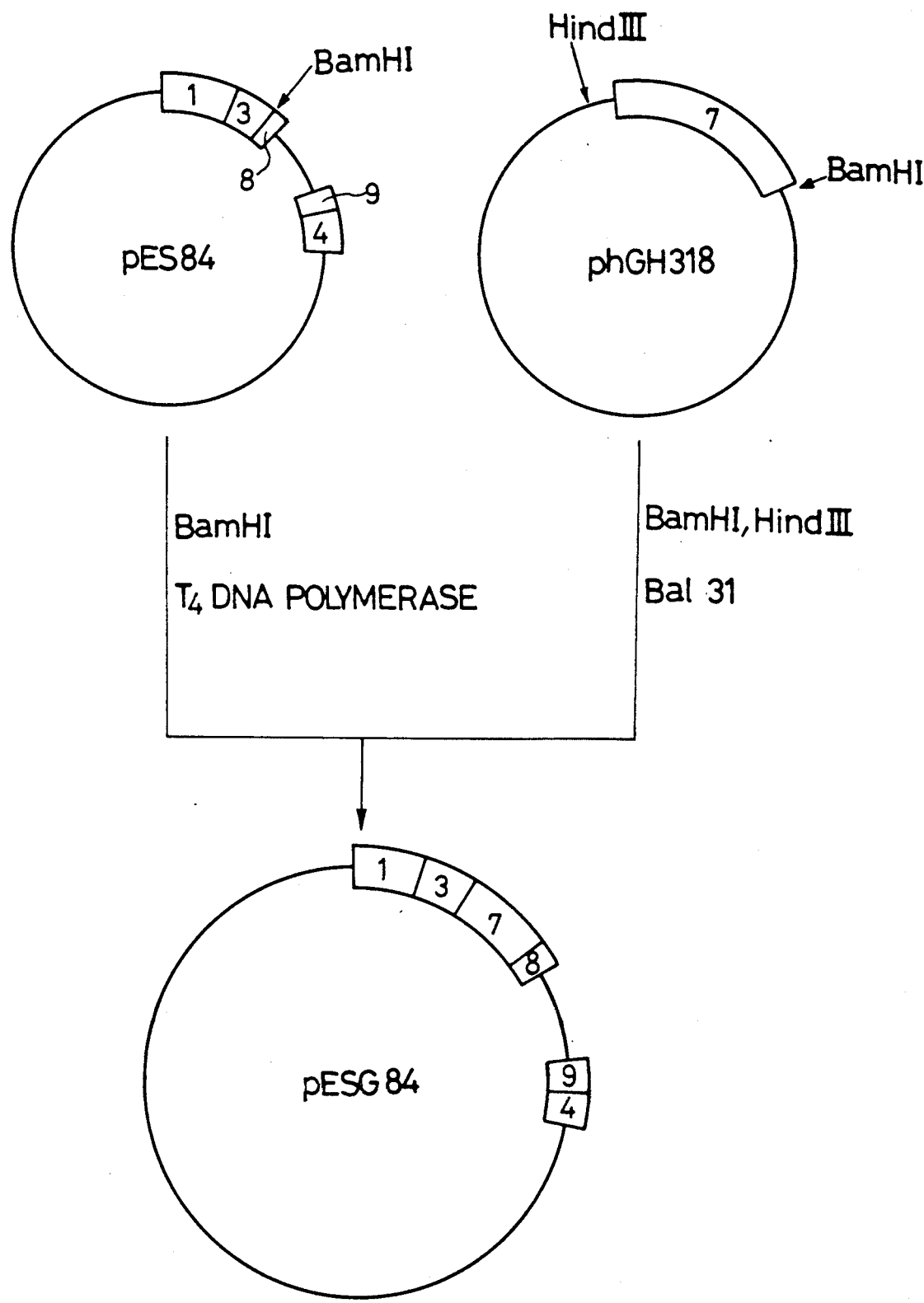
FIG. 8 is a drawing illustrating the procedure for creating the recombinant DNA molecule pESG 84.

Since the DNA fragment B also contained DNA sequences other than the human growth hormone gene, it is necessary to remove the DNA sequences other than the human growth hormone gene from the DNA fragment B in order to express the human growth hormone gene and secrete the human growth hormone thus expressed by using the expression-secretion vector pES84 of the present invention. Then, a DNA fragment of about 700 base pairs comprising the DNA fragment B deprived of the DNA sequences other than the human growth hormone gene (hereinafter referred to as DNA fragment C) was prepared, as shown in FIG. 8, by reacting the DNA fragment B (1 μg) with 10 units of exonuclease Bal31 (Takara Shuzo Co.) at 10° C. for one minute (the reaction system was the same as that used in the Bal31 treatment in Example 1).

Then, 0.1 μg of the DNA fragment C and 0.1 μg of the expression-secretion vector pES84 which had been cleaved completely with the restriction endonuclease BamHI were reacted using the $T_4$ DNA ligase of *Escherichia coli* (Takara Shuzo Co.) to prepare a recombinant DNA molecule (the reaction conditions and the composition of the reaction system were the same as those employed in joining the DNA fragment A with the double-stranded DNA in Example 2).

Using the recombinant DNA molecule thus obtained, *Bacillus subtilis* strain MT-0207 was transformed according to the protoplast method (stated above) to obtain transformed strains. Then, the transformed strains were shake cultured in the Penassay medium (Difco) at 30° C. for 16 hours and the cells were separated from the supernatant of the culture medium by centrifugation. The assay for the immunoactivity of the human growth hormone contained in the supernatant of the culture medium was made by the enzyme-immunoassay method (stated above) using an antiserum against human growth hormone. An immunoactivity to human growth hormone was observed in the supernatant of the culture medium of the transformed strain (*Bacillus subtilis* strain MT-8402, a stock of this strain was deposited on Oct. 14, 1985 under deposition No. FERM-BP-925 in accordance with the Budapest Treaty with FRI mentioned above). The level of secretion of human growth hormone was 10 mg/l.

Then, a recombinant DNA molecule (pESG84) was prepared from the transformed strain producing human growth hormone according to the alkaline method and thereafter, the restriction endonuclease map of pESG84 was constructed. As a result, it was confirmed that the recombinant DNA molecule (pESG84) obtained . from the transformed strain producing and secreting human growth hormone was a recombinant DNA molecule comprising the expression-secretion vector pES84 of the present invention and the human growth hormone gene (the DNA fragment C stated above).

EXAMPLE 5

Construction of a recombinant DNA molecule phGH928 coding for a definite junction region of the prepro-peptide and human growth hormone protein produced thereby and expression of a human growth hormone gene in *Bacillus subtilis* and secretion of the human growth hormone thus expressed using the recombinant DNA molecule phGH928

Figure 9:
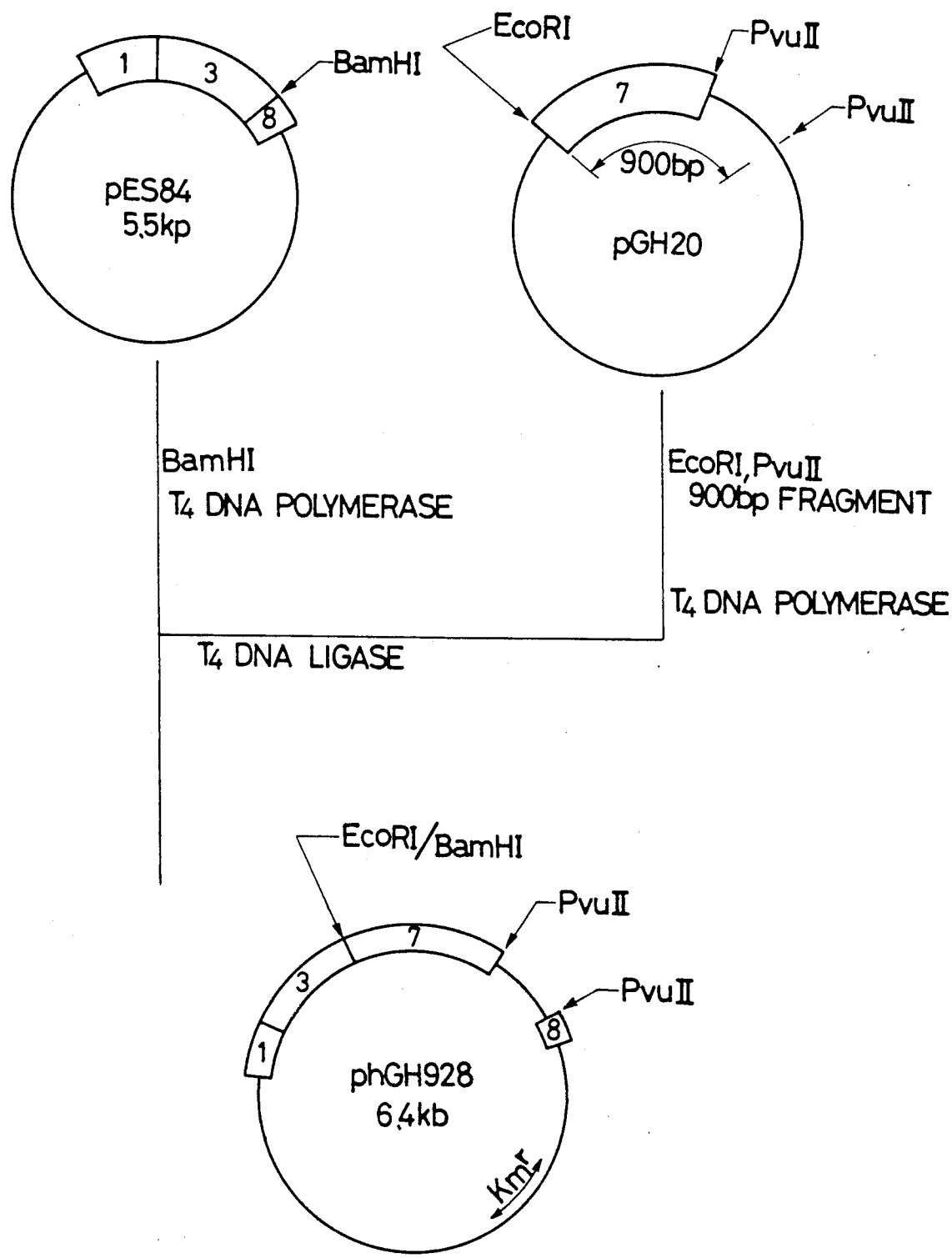
FIG. 9 is a drawing illustrating the procedure for creating the recombinant DNA molecule phGH 928.
Figure 11:
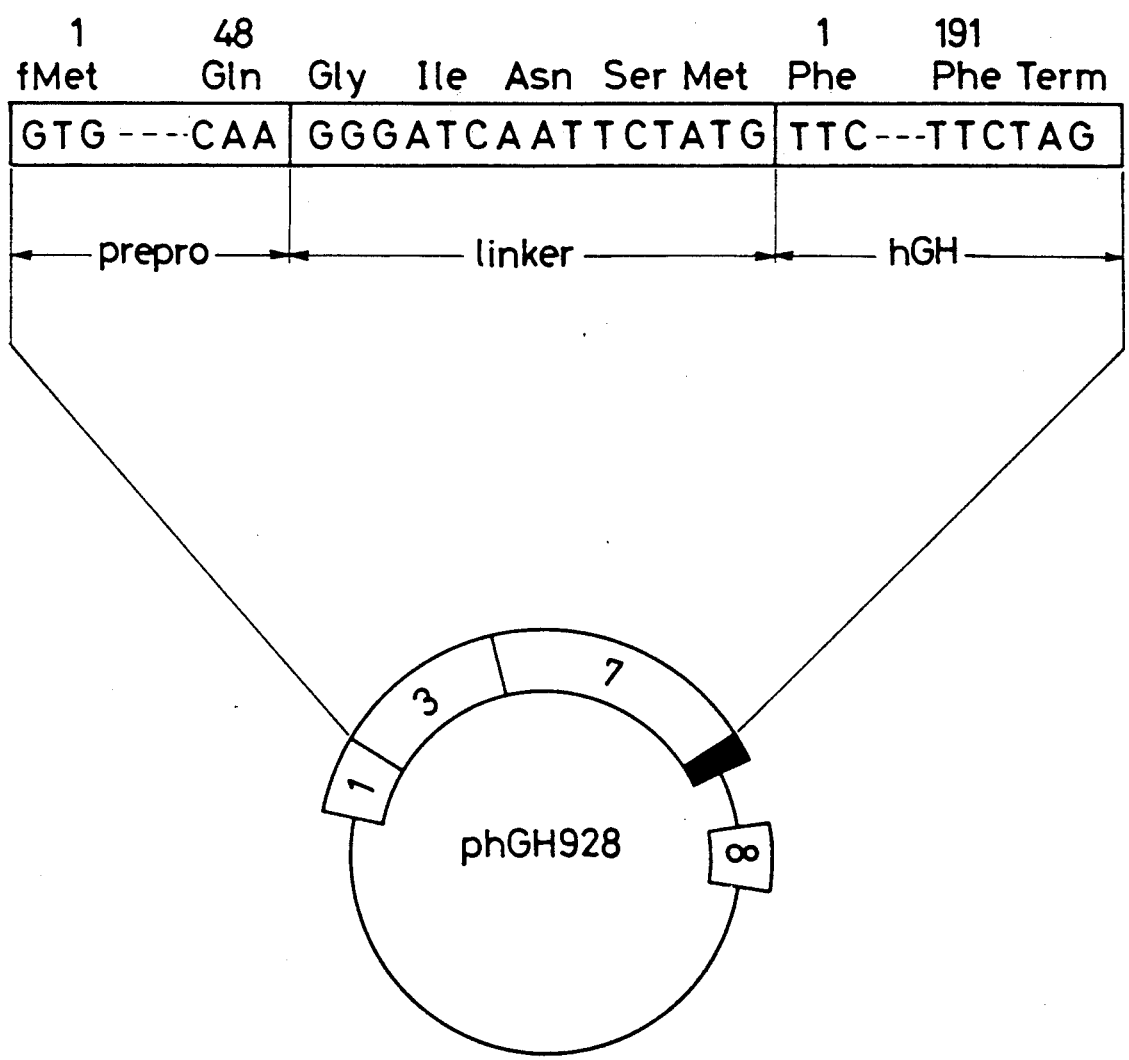
FIG. 11 is a drawing illustrating the recombinant DNA molecule phGH 928.

Since it was confirmed in Example 4 that the human growth hormone could be secreted in the culture medium by *Bacillus subtilis* by using the expression-secretion vector pES84, a recombinant DNA molecule, which codes for a definite amino acid sequence in the junction region of prepro-peptide and the human growth hormone as illustrated in FIG. 11, was then constructed in accordance with the procedure shown in FIG. 9 in the following manner, thereby attempting the production and secretion of human growth hormone by *Bacillus subtilis*. It was expected by this procedure to produce and secrete a tremendous amount of near-mature human growth hormone.

The human growth hormone gene was prepared using plasmid phGH20 containing said gene. Specifically, the plasmid phGH20 was cleaved with the endonucleases EcoRI (Takara Shuzo Co.) and PvuII (Takara Shuzo Co.) in the usual manner to prepare a DNA fragment (D) containing the DNA sequence comprising about 900 base pairs and coding for human growth hormone. Thereafter, the both ends of the DNA fragment were treated with T4 DNA polymerase (Takara Shuzo Co.) to generate flush ends.

Then, pES84 obtained in Example 3 was cleaved with the restriction endonuclease BamHI (Takara Shuzo Co.) and the both ends thereof thus obtained was treated with T4 DNA polymerase (Takara Shuzo Co.) to generate flush ends, thereby obtaining a DNA fragment (hereinafter referred to as DNA fragment E) (the composition of the reaction system and the reaction conditions were the same as those described above). The DNA fragment E (0.1 μg) thus obtained and the DNA fragment D (0.1 μg) were reacted using the T4 DNA ligase of *Escherichia coli* (Takara Shuzo Co.) to prepare a recombinant DNA molecule (the reaction conditions and the composition of the reaction system were the same as those used in joining the DNA segment A and the double-stranded DNA in Example 2).

Using the recombinant DNA molecule thus obtained, *Bacillus subtilis* strain MT-0207 was transformed according to the protoplast method (stated above) to obtain transformed strain: (*Bacillus subtilis* strain MT0928: a stock of this strain was deposited on Nov. 29, 1985 under deposition No. FERM BP-944 in accordance with the Budapest Treaty with FRI mentioned above). Then, the transformed strain (MT-0928) was shake cultured at 30° C. for 16 hours in the Penassay medium (Difco) and thereafter the cells were separated from the supernatant of the culture medium by centrifugation. The assay for the immunoactivity of the human growth hormone contained in the supernatant of the culture medium was made by the enzyme-immunoassay method (stated above) using an antiserum against human growth hormone. An immunoactivity to human growth hormone was observed in the supernatant of the culture medium of the transformant (*B. subtilis* strain MT-0928). The level of its secretion was 30 mg/l.

It was confirmed that the recombinant DNA molecule prepared from the transformant (*B. subtilis* strains MT-0928) was that shown in FIG. 10 (named phGH928). The nucleotide sequence of phGH928 DNA was determined according to the Maxam-Gilbert method (stated above). As a result, it was found that the recombinant DNA molecule phGH928 is a recombinant DNA molecule containing a DNA fragment in which the DNA sequence coding for human growth hormone was joined to the DNA sequence involved in the expression of a gene and the secretion of the protein thus expressed on its downstream side with the aid of a synthetic DNA linker.

What is claimed is:

1. A DNA fragment consisting essentially of the following regions of the extracellular neutral protease gene of *Bacillus amyloliquefaciens:*
   (a) a DNA sequence comprising a promoter and a ribosome binding region; and
   (b) a DNA sequence consisting of 5' portion of the prepro-peptide coding region;
   said DNA fragment being useful in the construction of an expression-secretion vector in the host bacterium of the genus Bacillus to provide improved secretion of heterologous protein, said DNA fragment having the following nucleotide sequence;

GATCTTAACA TTTTTCCCCT ATCATTTTTC

CCGTCTTCAT TTGTCATTTT TTCCAGAAAA

AATCGTCATT CGACTCATGT CTAATCCAAC

ACGTCTCTCT CGGCTTATCC CCTGACACCG

CCCGCCGACA GCCCGCATGG ACGAATCTAT

CAATTCAGCC GCGGAGTCTA GTTTTATATT

GCAGAATGCG AGATTGCTGG TTTATTATAA

CAATATAAGT TTTCATTATT TTCAAAAAGG

GGGATTTATT GTGGGTTTAG GTAAGAAATT

-continued

GTCTAGTGCT GTAGCCGCTT CCTTTATGAG

TTTAACCATC AGTCTGCCGG GTGTTCAGGC

CGCTGAGAAT CCTCAGCTTA AAGAAAACCT

GACGAATTTT GTACCGAAGC ATTCTTTGGT

GCAA.

2. A DNA fragment as claimed in claim 1 wherein a linker is joined to the 3' end of said 5'-region, said linker having at least one restriction endonuclease cleavage site through which a gene coding for a desired protein can be inserted and linked to the 3' end of said 5'-region.

3. A DNA fragment consisting essentially of the following regions of the extracellular neutral protease gene of *Bacillus amyloliquefaciens*:
   (a) a DNA sequence comprising a promoter and a ribosome binding region; and
   (b) a DNA sequence consisting of 5' portion of the prepro-peptide coding region;
   said DNA fragment being useful in the construction of an expression-secretion vector in the host bacterium of the genus Bacillus to provide improved secretion of a heterologous protein, wherein a linker is joined to the 3' end of said 5'-portion, said linker having at least one restriction endonuclease cleavage site through which a gene coding for a desired protein can be inserted and linked to the 3' end of said 5'-portion, said DNA fragment having the following nucleotide sequence:

GATCTTAACA TTTTTCCCCT ATCATTTTTC

CCGTCTTCAT TTGTCATTTT TTCCAGAAAA

AATCGTCATT CGACTCATGT CTAATCCAAC

ACGTCTCTCT CGGCTTATCC CCTGACACCG

CCCGCCGACA GCCCGCATGG ACGAATCTAT

CAATTCAGCC GCGGAGTCTA GTTTTATATT

GCAGAATGCG AGATTGCTGG TTTATTATAA

CAATATAAGT TTTCATTATT TTCAAAAAGG

-continued

GGGATTTATT GTGGGTTTAG GTAAGAAATT

GTCTAGTGCT GTAGCCGCTT CCTTTATGAG

TTTAACCATC AGTCTGCCGG GTGTTCAGGC

CGCTGAGAAT CCTCAGCTTA AAGAAAACCT

GACGAATTTT GTACCGAAGC ATTCTTTGGT

GCAA.

4. A DNA fragment consisting essentially of the following regions of the extracellular neutral protease gene of *Bacillus amyloliquefaciens*:
   (a) a DNA sequence comprising a promoter and a ribosome binding region; and
   (b) a DNA sequence consisting of 5' portion of the prepro-peptide coding region;
   said DNA fragment being useful in the construction of an expression-secretion vector in the host bacterium of the genus Bacillus to provide improved secretion of a heterologous protein, wherein a linker is joined to the 3' end of said 5'-portion, said linker having at least one restriction endonuclease cleavage site through which a gene coding for a desired protein can be inserted and linked to the 3' end of said 5'-portion, said DNA fragment having the following nucleotide sequence:

GATCTTAACA TTTTTCCCCT ATCATTTTTC CCGTCTTCAT TTGTCATTTT

TTCCAGAAAA AATCGTCATT CGACTCATGT CTAATCCAAC ACGTCTCTCT

CGGCTTATCC CCTGACACCG CCCGCCGACA GCCCGCATGG ACGAATCTAT

CAATTCAGCC GCGGAGTCTA GTTTTATATT GCAGAATGCG AGATTGCTGG

TTTATTATAA CAATATAAGT TTTCATTATT TTCAAAAAGG GGGATTTATT

GTGGGTTTAG GTAAGAAATT GTCTAGTGCT GTAGCCGCTT CCTTTATGAG

TTTAACCATC AGTCTGCCGG GTGTTCAGGC CGCTGAGAAT CCTCAGCTTA

AAGAAAACCT GACGAATTTT GTACCGAAGC ATTCTTTGGT GCAAGGGATC

C.

5. A DNA fragment consisting essentially of:
   (a) a DNA sequence comprising a promoter and a ribosome binding region; and
   (b) a DNA sequence consisting of 5' region of a prepro-peptide coding region, wherein the prepro-peptide coding region comprises the prepro-peptide coding region of plasmid pNPA 84, plasmid pNPA 58 or plasmid pNPA 86 and said coding region having base pairs omitted from its 3'-end, all said regions being essentially those of the extracellular neutral protease gene of *Bacillus amyloliquefaciens*,
   said DNA fragment being useful in the construction of an expression-secretion vector in the host bacterium of the genus Bacillus, to provide improved secretion of a heterologous protein.

6. A DNA fragment as claimed in claim 5 having the following nucleotide sequence:

GATCTTAACA TTTTTCCCCT ATCATTTTTC CCGTCTTCAT TTGTCATTTT

TTCCAGAAAA AATCGTCATT CGACTCATGT CTAATCCAAC ACGTCTCTCT

CGGCTTATCC CCTGACACCG CCCGCCGACA GCCCGCATGG ACGAATCTAT

```
CAATTCAGCC  GCGGAGTCTA  GTTTTATATT  GCAGAATGCG  AGATTGCTGG

TTTATTATAA  CAATATAAGT  TTTCATTATT  TTCAAAAAGG  GGGATTTATT

GTGGGTTTAG  GTAAGAAATT  GTCTAGTGCT  GTAGCCGCTT  CCTTTATGAG

TTTAACCATC  AGTCTGCCGG  GTGTTCAGGC  CGCTGAGAAT  CCTCAGCTTA

AAGAAAACCT  GACGAATTTT  GTACCGAAGC  ATTCTTTGGT  GCAA.
```

7. A DNA fragment as claimed in claim 5 wherein a linker is joined to the 3' end of said 5'-region, said linker having at least one restriction endonuclease cleavage site through which a gene coding for a desired protein can be inserted and linked to the 3' end of said 5'-region.

8. A DNA fragment as claimed in claim 7 having the following nucleotide sequence:

```
GATCTTAACA  TTTTTCCCCT  ATCATTTTTC  CCGTCTTCAT  TTGTCATTTT

TTCCAGAAAA  AATCGTCATT  CGACTCATGT  CTAATCCAAC  ACGTCTCTCT

CGGCTTATCC  CCTGACACCG  CCCGCCGACA  GCCCGCATGG  ACGAATCTAT

CAATTCAGCC  GCGGAGTCTA  GTTTTATATT  GCAGAATGCG  AGATTGCTGG

TTTATTATAA  CAATATAAGT  TTTCATTATT  TTCAAAAAGG  GGGATTTATT

GTGGGTTTAG  GTAAGAAATT  GTCTAGTGCT  GTAGCCGCTT  CCTTTATGAG

TTTAACCATC  AGTCTGCCGG  GTGTTCAGGC  CGCTGAGAAT  CCTCAGCTTA

AAGAAAACCT  GACGAATTTT  GTACCGAAGC  ATTCTTTGGT  GCAA.
```

9. A DNA fragment as claimed in claim 7 having the following nucleotide sequence:

```
GATCTTAACA  TTTTTCCCCT  ATCATTTTTC  CCGTCTTCAT  TTGTCATTTT

TTCCAGAAAA  AATCGTCATT  CGACTCATGT  CTAATCCAAC  ACGTCTCTCT

CGGCTTATCC  CCTGACACCG  CCCGCCGACA  GCCCGCATGG  ACGAATCTAT

CAATTCAGCC  GCGGAGTCTA  GTTTTATATT  GCAGAATGCG  AGATTGCTGG

TTTATTATAA  CAATATAAGT  TTTCATTATT  TTCAAAAAGG  GGGATTTATT

GTGGGTTTAG  GTAAGAAATT  GTCTAGTGCT  GTAGCCGCTT  CCTTTATGAG

TTTAACCATC  AGTCTGCCGG  GTGTTCAGGC  CGCTGAGAAT  CCTCAGCTTA

AAGAAAACCT  GACGAATTTT  GTACCGAAGC  ATTCTTTGGT  GCAAGGGATC
```
C.

10. An expression-secretion vector comprising:
   (a) a DNA sequence comprising a promoter region, a ribosome binding region and a 5'-region of a prepro-peptide coding region, wherein the prepropeptide coding region comprises the prepro-peptide coding region of plasmid pNPA 84, plasmid pNPA 58 or plasmid pNPA 86 and said coding region having base pairs omitted from its 3'-end, all said regions being essentially those of the extracellular neutral protease gene of Bacillus amyloliquefaciens;
   (b) a vector DNA derived from a plasmid or a phage capable of replicating in a host bacterium of the genus Bacillus; and
   (c) a linker joined to the 3' end of said 5'-region, said linker having one or more restriction endonuclease cleavage sites through which a gene coding for a desired protein can be inserted and linked to the 3' end of the DNA sequence (a) so that the expression and secretion of the desired protein is directed by the DNA sequence (a).

11. An expression-secretion vector as claimed in claim 10 wherein the DNA sequence (a) has the following nucleotide sequence:

```
GATCTTAACA  TTTTTCCCCT  ATCATTTTTC

CCGTCTTCAT  TTGTCATTTT  TTCCAGAAAA

AATCGTCATT  CGACTCATGT  CTAATCCAAC

ACGTCTCTCT  CGGCTTATCC  CCTGACACCG

CCCGCCGACA  GCCCGCATGG  ACGAATCTAT

CAATTCAGCC  GCGGAGTCTA  GTTTTATATT

GCAGAATGCG  AGATTGCTGG  TTTATTATAA

CAATATAAGT  TTTCATTATT  TTCAAAAAGG

GGGATTTATT  GTGGGTTTAG  GTAAGAAATT

GTCTAGTGCT  GTAGCCGCTT  CCTTTATGAG

TTTAACCATC  AGTCTGCCGG  GTGTTCAGGC

CGCTGAGAAT  CCTCAGCTTA  AAGAAAACCT
```

-continued

GACGAATTTT GTACCGAAGC ATTCTTTGGT

GCAA.

12. An expression-secretion vector as in claim 11, wherein the linker is represented by the following nucleotide sequence:

5' GGGATCC 3'.

13. An expression-secretion vector as claimed in claim 12, which is pES 84.

14. An expression-secretion vector as claimed in claim 10, wherein the DNA sequence is derived from plasmid pUB110.

15. A recombinant DNA molecular comprising:
  (a) a DNA sequence comprising a promoter region, a ribosome binding region and a 5'-region of a pre-pro-peptide coding region, wherein the prepropeptide coding region comprises the prepro-peptide coding region of plasmid pNPA 84, plasmid pNPA 58 or plasmid pNPA 86 and said coding region having base pairs omitted from its 3'-end, all said regions being essentially those of the extracellular neutral protease gene of *Bacillus amyloliquefaciens;*
  (b) a vector DNA derived from a plasmid or a phage capable of replicating in a host bacterium of the genus Bacillus; and
  (c) a linker joined to the 3' end of said 5'-region through a linker so that the expression and secretion of the desired protein is directed by the DNA sequence (a).

16. A recombinant DNA molecule as claimed in claim 15, wherein the DNA sequence (a) has the following nucleotide sequence:

GATCTTAACA TTTTTCCCCT ATCATTTTTC

CCGTCTTCAT TTGTCATTTT TTCCAGAAAA

AATCGTCATT CGACTCATGT CTAATCCAAC

ACGTCTCTCT CGGCTTATCC CCTGACACCG

CCCGCCGACA GCCCGCATGG ACGAATCTAT

CAATTCAGCC GCGGAGTCTA GTTTTATATT

GCAGAATGCG AGATTGCTGG TTTATTATAA

CAATATAAGT TTTCATTATT TTCAAAAAGG

GGGATTTATT GTGGGTTTAG GTAAGAAATT

GTCTAGTGCT GTAGCCGCTT CCTTTATGAG

TTTAACCATC AGTCTGCCGG GTGTTCAGGC

CGCTGAGAAT CCTCAGCTTA AGAAAACCT

GACGAATTTT GTACCGAAGC ATTCTTTGGT

GCAA.

17. A recombinant DNA molecule as claimed in claim 16, wherein the desired protein is human interferon-β.

18. A recombinant DNA molecule as claimed in claim 16, which is pESI 84.

19. A recombinant DNA molecule as claimed in claim 16, wherein the desired protein is human growth hormone.

20. A recombinant DNA molecule as claimed in claim 16, which is pESG 84 or phGH 84.

21. A method for producing a desired protein, comprising the steps of:
  (a) transforming a host bacterium of the genus Bacillus with a recombinant DNA molecule as claimed in claim 16,
  (b) culturing the resultant transformant in a culture medium to secrete the desired protein by expression of a gene for a protein encoded by the recombinant DNA molecule; and
  (c) recovering the secreted protein from the culture medium.

22. An expression-secretion vector, comprising:
  (a) a DNA sequence comprising a promoter region, a ribosome binding region and a 5'-region having a length within the range of 144 to 190 bases of a prepro-peptide coding region, said coding region having base pairs omitted from its 3'-end, all said regions being essentially those of the extracellular neutral protease gene of *Bacillus amyloliquefaciens;*
  (b) a vector DNA derived from a plasmid or a phage capable of replicating in a host bacterium of the genus Bacillus; and
  (c) a linker joined to the 3' end of said 5'-region, said linker having one or more restriction endonuclease cleavage sites through which a gene coding for a desired protein can be inserted and linked to the 3' end of the DNA sequence (a) so that the expression and secretion of the desired protein is directed by the DNA sequence (a), wherein the expression-secretion vector is pNPA 86 or pNPA 58.

23. An expression-secretion vector, comprising:
  (a) a DNA sequence comprising a promoter region, a ribosome binding region and a 5'-region having a length within the range of 144 to 190 bases of a prepro-peptide coding region, said coding region having base pairs omitted from its 3'-end, all said regions being essentially those of the extracellular neutral protease gene of *Bacillus amyloliquefaciens;*
  (b) a vector DNA derived from a plasmid or a phage capable of replicating in a host bacterium of the genus Bacillus; and
  (c) a linker joined to the 3' end of said 5'-region, said linker having one or more restriction endonuclease cleavage sites through which a gene coding for a desired protein can be inserted and linked to the 3' end of the DNA sequence (a) so that the expression and secretion of the desired protein is directed by the DNA sequence (a), wherein the DNA sequence (a) has the following nucleotide sequence:

GATCTTAACA TTTTTCCCCT ATCATTTTTC

CCGTCTTCAT TTGTCATTTT TTCCAGAAAA

AATCGTCATT CGACTCATGT CTAATCCAAC

ACGTCTCTCT CGGCTTATCC CCTGACACCG

CCCGCCGACA GCCCGCATGG ACGAATCTAT

CAATTCAGCC GCGGAGTCTA GTTTTATATT

GCAGAATGCG AGATTGCTGG TTTATTATAA

CAATATAAGT TTTCATTATT TTCAAAAAGG

-continued

```
GGGATTTATT GTGGGTTTAG GTAAGAAATT
GTCTAGTGCT GTAGCCGCTT CCTTTATGAG
TTTAACCATC AGTCTGCCGG GTGTTCAGGC
CGCTGAGAAT CCTCAGCTTA AAGAAAACCT
GACGAATTTT GTACCGAAGC ATTCTTTGGT
GCAA.
```

24. An expression-secretion vector as claimed in claim 23, which is pNPA 84.

25. An expression-secretion vector as claimed in claim 23, wherein the linker is represented by the following nucleotide sequence:

5' GGGATCC 3'.

26. An expression-secretion vector as claimed in claim 25, which is pES 84.

27. An expression-secretion vector as claimed in claim 23, wherein the DNA fragment is derived from plasmid pUB110.

28. An recombinant DNA molecule comprising:
(a) a DNA sequence comprising a promoter region, a ribosome binding region and a 5'-region having a length within the range of 144 to 190 bases of a prepro-peptide coding region, said coding region having base pairs omitted from its 3'-end, all said regions being essentially those of the extracellular neutral protease gene of *Bacillus amyloliquefaciens*;
(b) a vector DNA derived from a plasmid or a phage capable of replicating in a host bacterium of the genus Bacillus; and
(c) a gene for a desired protein linked to the 3' end of said 5'-region through a linker so that the expression and secretion of the desired protein is directed by the DNA sequence (a), wherein the DNA sequence (a) has the following nucleotide sequence:

```
GATCTTAACA TTTTTCCCCT ATCATTTTTC
CCGTCTTCAT TTGTCATTTT TTCCAGAAAA
AATCGTCATT CGACTCATGT CTAATCCAAC
ACGTCTCTCT CGGCTTATCC CCTGACACCG
CCCGCCGACA GCCCGCATGG ACGAATCTAT
CAATTCAGCC GCGGAGTCTA GTTTTATATT
GCAGAATGCG AGATTGCTGG TTTATTATAA
CAATATAAGT TTTCATTATT TTCAAAAAGG
GGGATTTATT GTGGGTTTAG GTAAGAAATT
GTCTAGTGCT GTAGCCGCTT CCTTTATGAG
TTTAACCATC AGTCTGCCGG GTGTTCAGGC
CGCTGAGAAT CCTCAGCTTA AAGAAAACCT
GACGAATTTT GTACCGAAGC ATTCTTTGGT
GCAA.
```

29. A recombinant DNA molecule as claimed in claim 28, wherein the desired protein is human interferon-β.

30. A recombinant DNA molecule as claimed in claim 28, which is pESI 84.

31. A recombinant DNA molecular as claimed in claim 28, wherein the desired protein is human growth hormone.

32. A recombinant DNA molecule as claimed in claim 28, which is pESG 84 or phGH 84.

33. A method for producing a desired protein comprising:
(a) transforming a host bacterium of the genus Bacillus with a recombinant DNA molecule as claimed in any one of claims 28, 29, 30, 31, and 32;
(b) culturing the resultant transformant in a culture medium to secrete the desired protein by expression of a gene for the protein encoded by the recombinant DNA molecule; and
(c) recovering the secreted protein from the culture medium.

* * * * *

UNITED STATES PATENT AND TRADEMARK OFFICE
CERTIFICATE OF CORRECTION

PATENT NO. : 5,015,574

DATED : May 14, 1991

INVENTOR(S) : Furutani et al.

It is certified that error appears in the above-identified patent and that said Letters Patent is hereby corrected as shown below:

On title page, item [73], "Assignees" should read --Assignee-- and the portion identifying the address "both of Tokyo, Japan" should read -- of Tokyo, Japan --.

Signed and Sealed this

First Day of March, 1994

Attest:

BRUCE LEHMAN

Attesting Officer

Commissioner of Patents and Trademarks